(12) United States Patent
Stanley et al.

(10) Patent No.: US 11,989,767 B2
(45) Date of Patent: May 21, 2024

(54) METHOD FOR IMAGE-BASED DISPOSABLE ARTICLE SIZING

(71) Applicant: The Procter & Gamble Company, Cincinnati, OH (US)

(72) Inventors: Scott K. Stanley, Mason, OH (US); Andrew P. Rapach, Fairfield, OH (US); Andrew J. Sauer, Cincinnati, OH (US); Alexander E. Unger, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 517 days.

(21) Appl. No.: 16/927,069

(22) Filed: Jul. 13, 2020

(65) Prior Publication Data

US 2021/0241352 A1   Aug. 5, 2021

Related U.S. Application Data

(60) Provisional application No. 62/968,201, filed on Jan. 31, 2020.

(51) Int. Cl.
*G06Q 30/0601* (2023.01)
*A61F 13/472* (2006.01)
(Continued)

(52) U.S. Cl.
CPC ....... *G06Q 30/0631* (2013.01); *A61F 13/472* (2013.01); *A61F 13/49* (2013.01); *A61F 13/496* (2013.01); *G06N 20/00* (2019.01); *G06Q 10/087* (2013.01); *G06Q 10/109* (2013.01); *G06Q 30/0621* (2013.01); *G06Q 30/0643* (2013.01); *G06T 7/62* (2017.01); *G16H 50/20* (2018.01);
(Continued)

(58) Field of Classification Search
CPC ............. G06Q 30/0631; G06Q 10/087; G06Q 10/109; G06Q 30/0621; G06Q 30/0643; A61F 13/472; A61F 13/49; A61F 13/496; G06N 20/00; G06T 7/62; G06T 2207/30196; G06T 7/60; G16H 50/20; G16H 50/30; G16H 10/20; G16H 30/20; G16H 30/40; G16H 40/67
See application file for complete search history.

(56) References Cited

U.S. PATENT DOCUMENTS

2014/0304256 A1   10/2014   Yankovich et al.
2016/0349738 A1*  12/2016   Sisk ................... G05B 19/4097
(Continued)

FOREIGN PATENT DOCUMENTS

WO   WO-2020004217 A1 *   1/2020

OTHER PUBLICATIONS

Stabelfeldt, S. (2004), Designing Diapers and Sizing Schemes with a Fit Mapping Tool. The IP.com Journal (Year: 2004).*
(Continued)

*Primary Examiner* — Jeffrey A. Smith
*Assistant Examiner* — Latasha D Ramphal
(74) *Attorney, Agent, or Firm* — Daniel S. Albrecht; C. Brant Cook

(57) ABSTRACT

Systems and methods for recommending a size of disposable article to be worn by a subject are provided. An image of the subject is analyzed to determine the subject's fit parameters. The fit parameters are applied to sizing models of various disposable articles.

25 Claims, 17 Drawing Sheets

(51) Int. Cl.
| | |
|---|---|
| *A61F 13/49* | (2006.01) |
| *A61F 13/496* | (2006.01) |
| *G06N 20/00* | (2019.01) |
| *G06Q 10/087* | (2023.01) |
| *G06Q 10/109* | (2023.01) |
| *G06T 7/62* | (2017.01) |
| *G16H 50/20* | (2018.01) |
| *G16H 50/30* | (2018.01) |

(52) U.S. Cl.
CPC ... *G16H 50/30* (2018.01); *G06T 2207/30196* (2013.01)

(56) References Cited

U.S. PATENT DOCUMENTS

2017/0249602 A1* 8/2017 Robertson .............. G06Q 10/30
2019/0347817 A1* 11/2019 Ferrantelli ............ G06F 18/217
2019/0371080 A1* 12/2019 Sminchisescu ......... G06T 17/20

OTHER PUBLICATIONS

International Search Report and Written Opinion; Application No. PCTUS2020/070259; dated Sep. 15, 2020; 14 pages.

\* cited by examiner

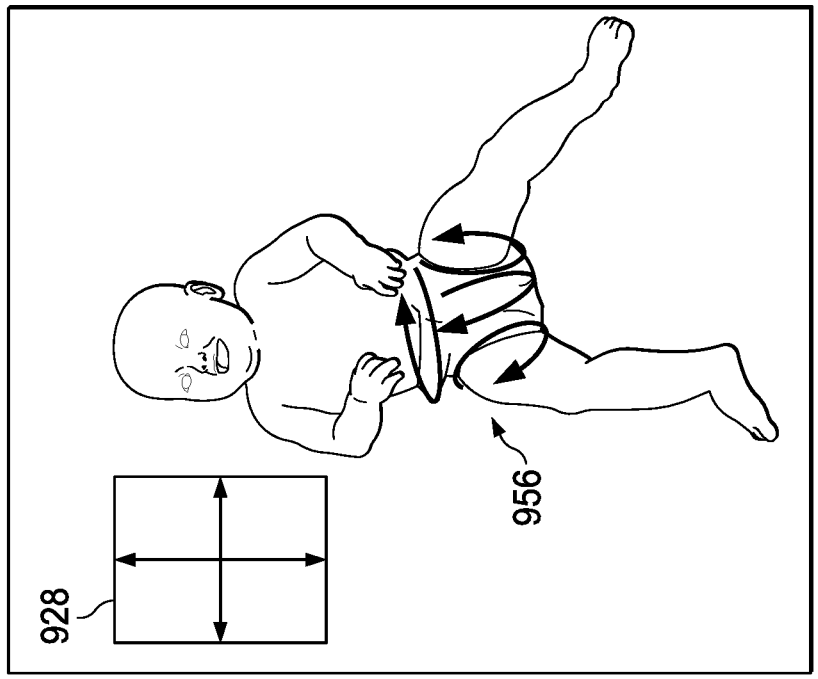
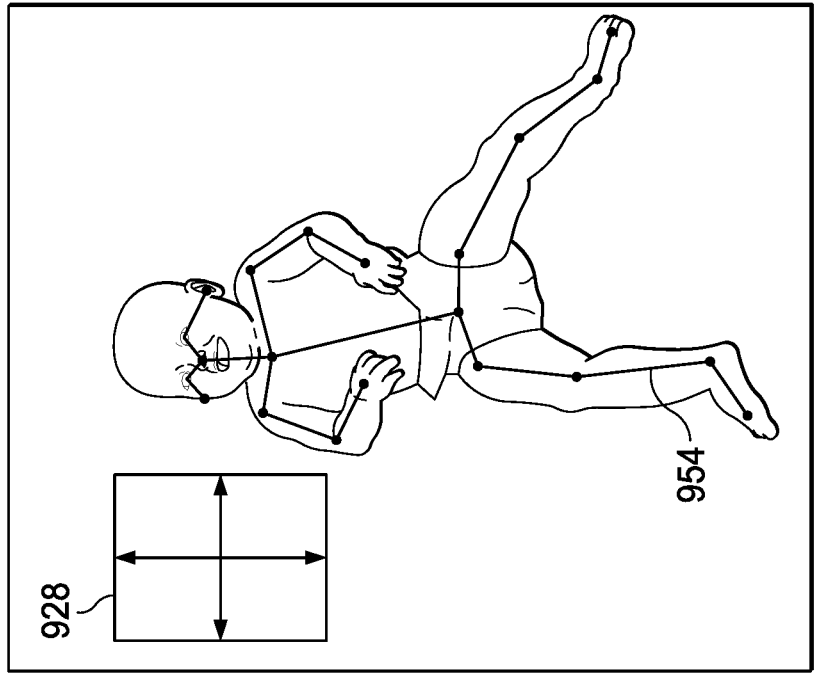
FIG. 9

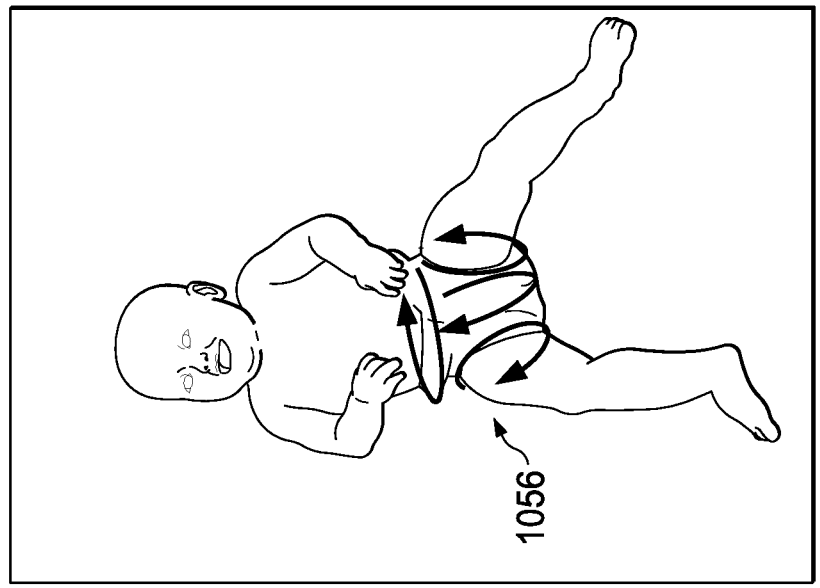
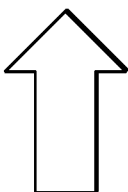
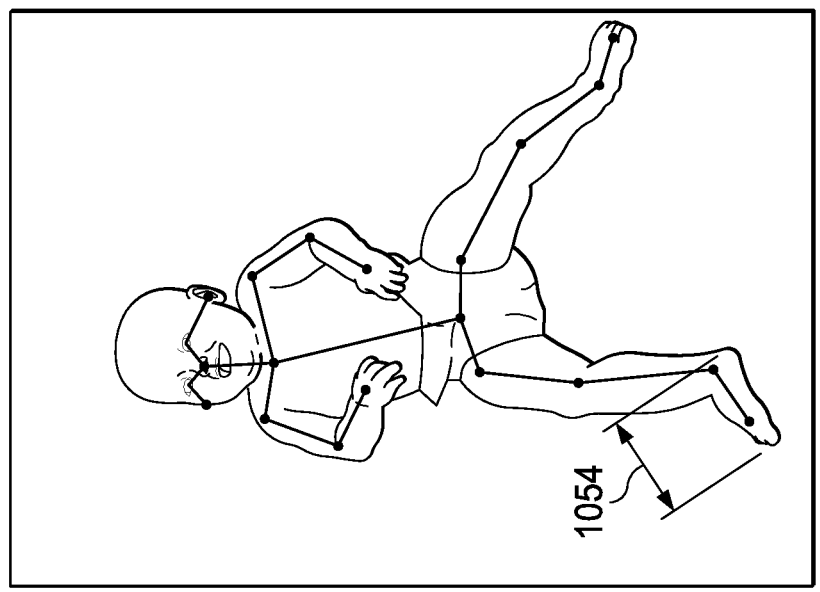
FIG. 10

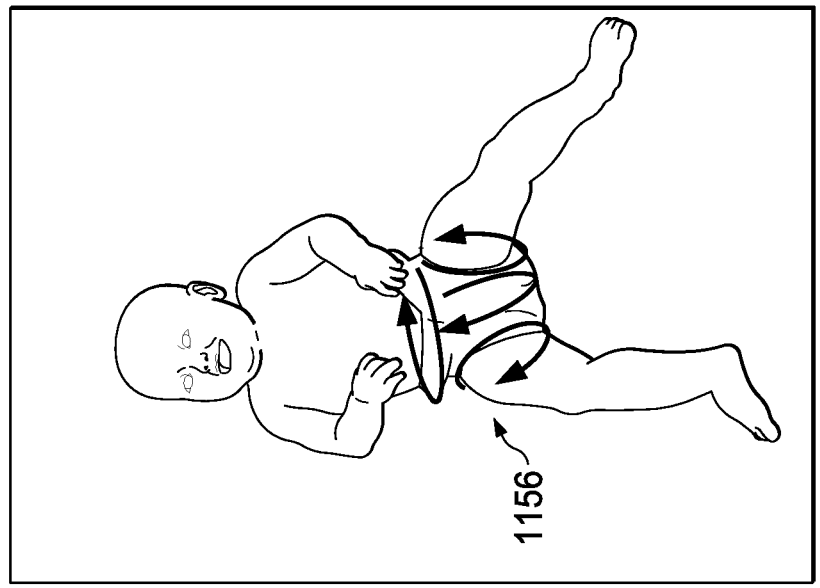
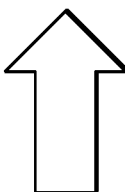
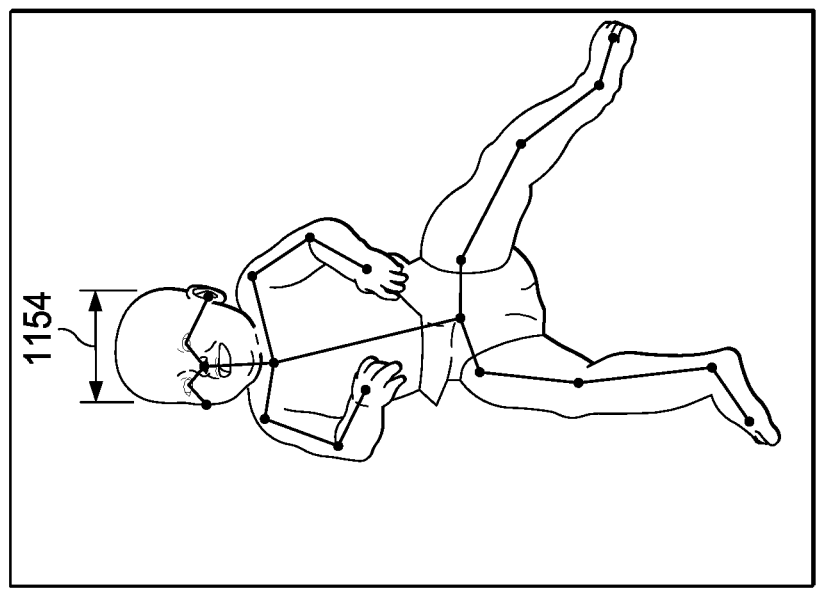
FIG. 11

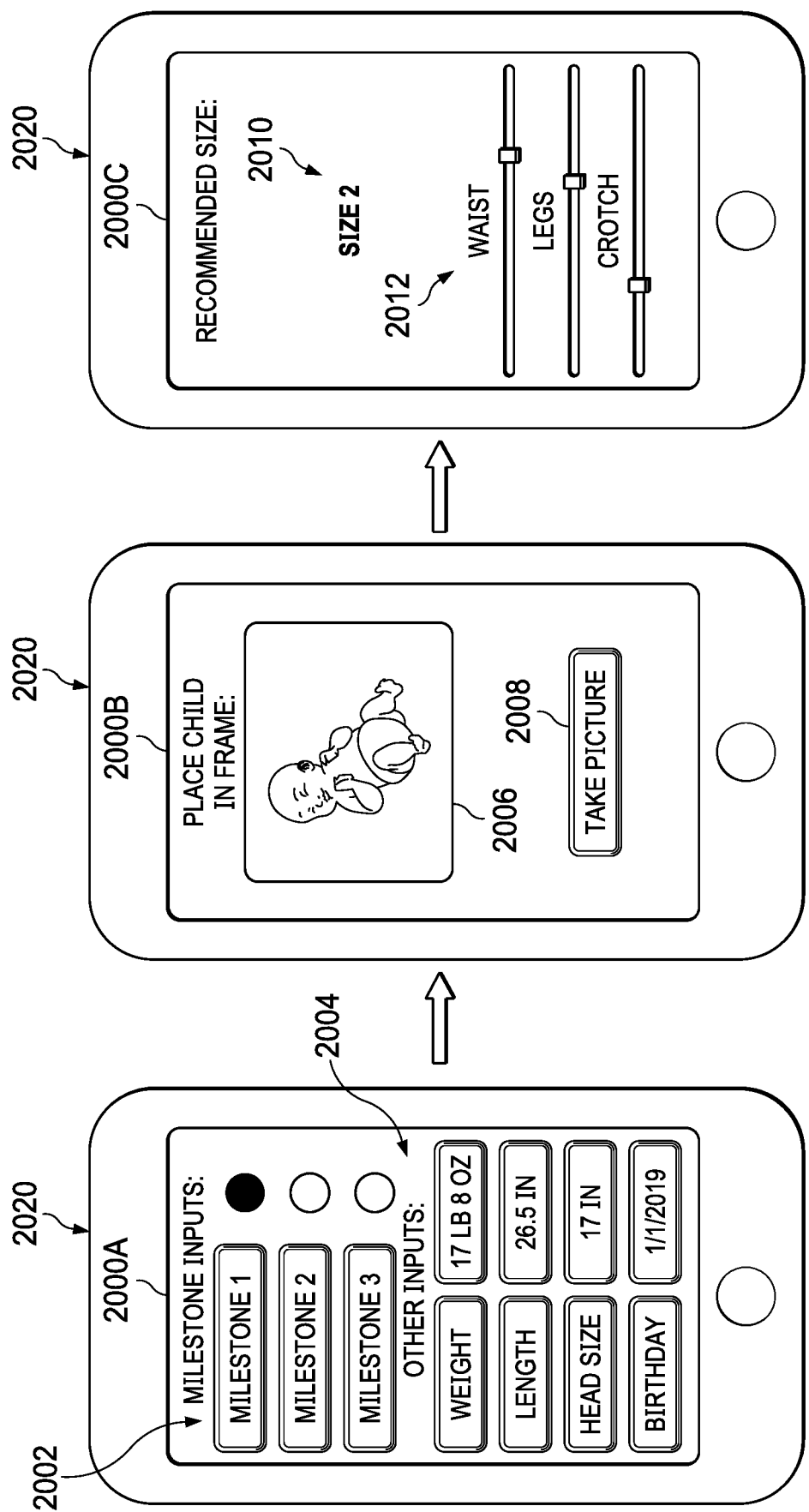

METHOD FOR IMAGE-BASED DISPOSABLE ARTICLE SIZING

FIELD OF THE INVENTION

The present disclosure relates to systems and methods for determining a recommended size of disposable article to be worn by a subject, and more particularly, systems and methods for determining a recommended size of disposable article to be worn by a subject based on the processing of an image of the subject.

BACKGROUND OF THE INVENTION

Absorbent articles, such as diapers, training pants, and the like, are manufactured in a variety of sizes and configurations. Wearing an appropriate size is important in order to ensure the absorbent article is comfortable and performs properly. With the numerous product lines available for purchase, and with each product line typically having a plurality of sizing options, it may be challenging to determine which product line and which size is well-suited for a particular wearer. Additionally, disposable article sizes are typically recommended based on a wearer's weight, as opposed to physical dimensions of the wearer. The wearer's weight, however, can be a poor predictor of the wearer's actual physical dimensions, so choosing product size on the wearer's weight can lead to improper fit. Further, while knowledge of the physical dimensions of the wearer is relevant for proper disposable article fit, the physical dimensions of the wearer are not typically known and can be difficult to manually measure. Therefore, there is a need for systems and methods for recommending absorbent articles based on the physical attributes of a wearer.

SUMMARY OF THE INVENTION

In one form, a computer-based method comprises storing, by a disposable article recommendation computing system in data store, a plurality of disposable article sizing models that correspond to a respective plurality of pre-made disposable articles available for purchase. The method further comprises receiving, by the disposable article recommendation computing system, an image collected by at least one camera, wherein the image comprises a representation of a subject and the subject is a consumer of pre-made disposable articles. The method further comprises determining, by the disposable article recommendation computing system, a scale of the image that correlates dimensions of the representation of the subject in the image to physical dimensions of the subject. The method further comprises determining, by the disposable article recommendation computing system, physical attributes of the representation of the subject in the image. The method further comprises determining, by the disposable article recommendation computing system, a plurality of fit parameters for the subject based on the scale of the image and the physical attributes of the representation of the subject. The method further comprises applying, by the disposable article recommendation computing system, the plurality of fit parameters to one or more of the plurality of disposable article sizing models. The method further comprises, based on the application of the plurality of fit parameters to the one or more of the plurality of disposable article sizing models, determining, by the disposable article recommendation computing system, a recommended pre-made disposable article for the subject, wherein the recommended pre-made disposable article is selected from the plurality of pre-made disposable articles available for purchase. The method further comprises providing, by the disposable article recommendation computing system, an indication of the recommended pre-made disposable article for the subject.

In another form, a computer-based system comprises a data store, wherein a plurality of disposable article sizing models that correspond to respective sizes of pre-made disposable articles available for purchase are stored by the data store. The system further comprises a disposable article recommendation computing system comprising computer-readable medium having computer-executable instructions stored thereon. The computer-executable instructions are configured to instruct one or more computer processors to receive an image of a subject collected by a remote mobile computing device, determine a scale of the image, and process the image to determine physical attributes of the subject. Based on the scale of the image and the physical attributes of the subject, a plurality of fit parameters for the subject are determined. The computer-executable instructions are further configured to instruct one or more computer processors to compare the plurality of fit parameters to one or more of the plurality of disposable article sizing models. Based on the comparison of the plurality of fit parameters to the one or more of the plurality of disposable article sizing models, a recommended pre-made disposable article for the subject is determined. The computer-executable instructions are configured to instruct one or more computer processors to send an indication of the recommended pre-made disposable article to the remote mobile computing device.

In another form, a computer-based method comprises storing a plurality of disposable article sizing models that correspond to a respective plurality of pre-made disposable articles available for purchase. The method further comprises receiving an image collected by at least one camera, wherein the image comprises a representation of a subject and the subject is a consumer of pre-made disposable articles. The method further comprises determining a scale of the image that correlates dimensions of the representation of the subject in the image to physical dimensions of the subject. The method further comprises determining physical attributes of the representation of the subject in the image through image processing. The method further comprises determining a plurality of fit parameters for the subject based on the scale of the image and the physical attributes of the representation of the subject. The method further comprises determining, by the disposable article recommendation computing system, a recommended pre-made disposable article for the subject based on an application of the plurality of fit parameters to the one or more of the plurality of disposable article sizing models, wherein the recommended pre-made disposable article is selected from the plurality of pre-made disposable articles available for purchase. The method further comprises providing, by the disposable article recommendation computing system, an indication of the recommended pre-made disposable article for the subject.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 9 depicts the determination of fit parameters of a subject using a scale object.

FIG. 10 depicts the determination of fit parameters of a subject using a foot dimension to determine scale.

FIG. 11 depicts the determination of fit parameters of a subject using a head circumference to determine scale.

FIG. 20 depicts a series of simplified interfaces for collecting various inputs from a user and displaying of a recommendation.

DETAILED DESCRIPTION OF THE INVENTION

Figure 1:
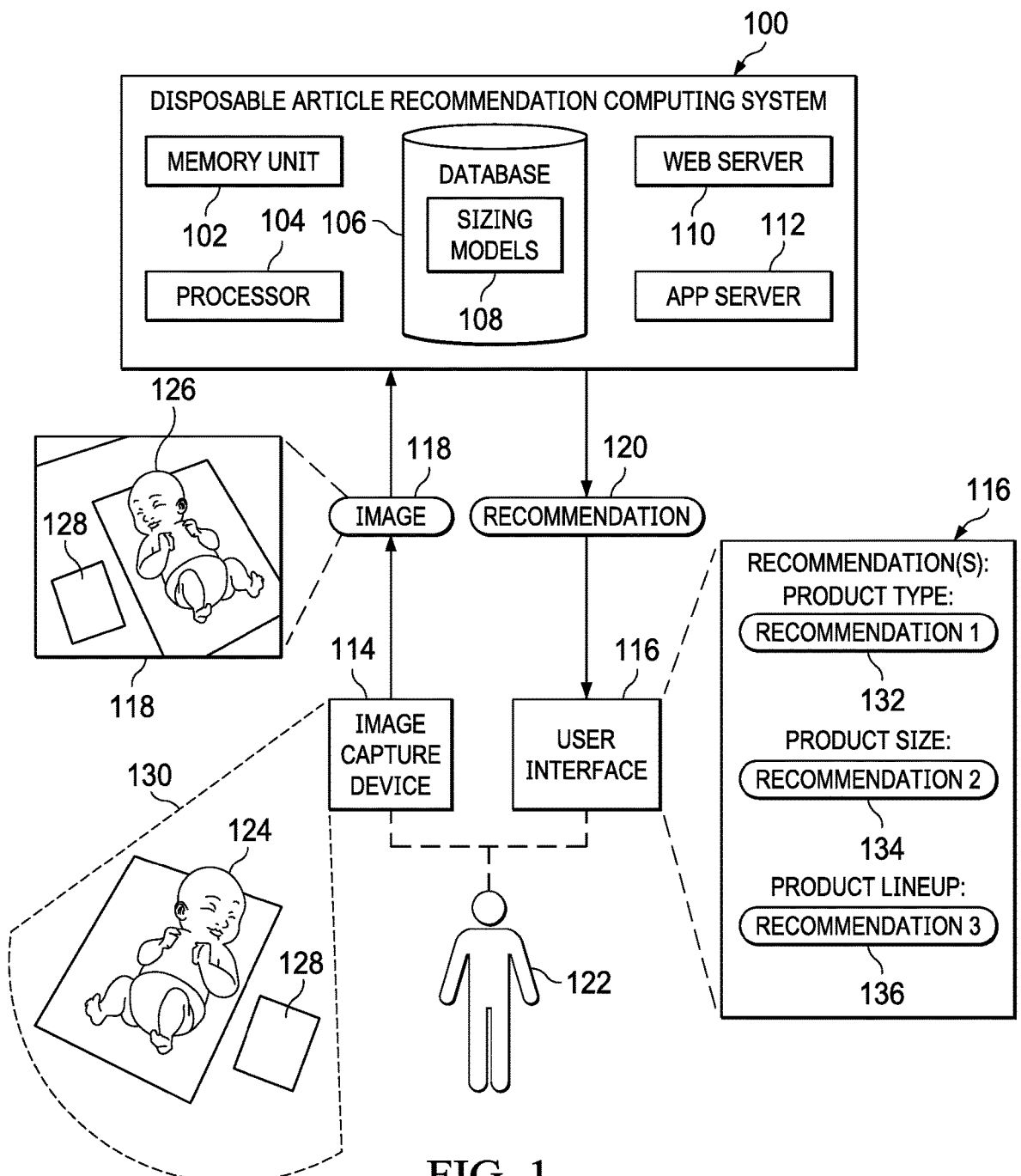
FIG. 1 depicts a user interacting with an example disposable article recommendation computing system.

The present disclosure relates to systems and processes for recommending a size of a disposable article based on the processing of an image to determine the physical attributes of the intended wearer. Various nonlimiting embodiments of the present disclosure will now be described to provide an overall understanding of the principles of the function, design and operation of the manufacturing systems and methods. One or more examples of these nonlimiting embodiments are illustrated in the accompanying drawings. Those of ordinary skill in the art will understand that the systems and methods described herein and illustrated in the accompanying drawings are nonlimiting example embodiments and that the scope of the various nonlimiting embodiments of the present disclosure are defined solely by the claims. The features illustrated or described in connection with one nonlimiting embodiment may be combined with the features of other nonlimiting embodiments. Such modifications and variations are intended to be included within the scope of the present disclosure.

The term "absorbent article," as used herein, refers to disposable devices such as infant, child, adult diapers, pant-style diapers, training pants, feminine hygiene products, and the like, which are placed against or in proximity to the body of the wearer to absorb and contain the various exudates discharged from the body. Typically, these articles comprise a topsheet, backsheet, an absorbent core, an acquisition system (which may be referred to as a liquid management system and may be comprised of one or several layers) and typically other components, with the absorbent core normally placed at least partially between the backsheet and the acquisition system or between the topsheet and the backsheet. The absorbent articles of the present disclosure will be further illustrated in the below description and in the figures in the form of a taped diaper. Nothing in this description should be, however, considered limiting to the scope of the claims. Instead, the present disclosure applies to any suitable form of absorbent articles (e.g., training pants, feminine hygiene products, adult incontinence products, etc.). For instance, the systems and methods described herein are applicable for use with a range of different absorbent article types, such as disposable, semi-durable, single use, multiple use, multi-part, cloth, pant, pull-up or insert types of absorbent articles and products. Absorbent articles in accordance with the present disclosure can be pre-made, such that they are manufactured in predetermined sizes that are configured to be worn by wearers having certain physical attributes. In some embodiments, absorbent articles in accordance with the present disclosure are at least partially customizable, such as that certain aspects can be configured based on the physical attributes of the intended wearer. By way of example, a leg hoop size of the absorbent article to worn by a particular wearer can be custom sized to provide that particular wearer with a better fit.

In some configurations, the systems and methods described herein can receive one or more digital images of a subject, and by way of various image processing techniques, determine physical attributes of the subject. The subject can be, for example, an infant, a baby, a toddler, or other wearer of an absorbent article. The particular physical attributes determined by the present systems and methods can vary based on implementation, but in some configurations, image analysis is performed to determine various fit parameters. Examples of fit parameters include an estimated waist circumference of the subject, an estimated thigh circumference of the subject, and an estimated rise measurement of the subject, as measured from naval to the lower back. The fit parameters can be applied to various sizing models of absorbent articles to assess which product or products would fit the subject. An absorbent article recommendation can then be provided for the subject. The recommendation can identify, for example, any of a product size, a product type, and a product line. In some configurations, additional information regarding the subject beyond the image can be used in determining the recommendation. Non-limiting examples of additional information regarding the subject that can be leveraged by the systems and methods described herein include, but are not limited to, the subject's age, the subject's gestational age, the subject's geographic location, and developmental milestone completion. Example developmental milestones can include, without limitation, crawling, pulling up on furniture, walking, commenced potty training, and so forth. Additionally or alternatively, dimensional information regarding the subject can be provided by a user, such as the subject's height, weight, head circumference, and so forth, which can be leveraged by the system in making an absorbent article recommendation. Additionally or alternatively, fit assessment or performance feedback regarding a currently used product can be provided as an input, as well as other use-based parameters such as number of bowel movement diapers per day or number of wet diapers per day. Additionally or alternatively, absorbent article preferences, such as preference for more natural product, preference for products suitable for more active children, preference for high absorbency or overnight products, and so forth, may be provided by a user and taken into consideration.

Other user-provided information may include, for example, whether the wearer is clothed or is only wearing a diaper or this information may be determined by an algorithm, for example. In any of the above examples, data associated with a user profile, or other user-provided information, may be utilized in determining a recommendation. Additionally or alternatively, data obtained from public growth chart databases may be utilized in determining a recommendation. Furthermore, the type of user-provided information utilized by the system can depend on the type of absorbent article being recommended. By way of example, for feminine hygiene product recommendations, user-provided information can include, without limitation, menstrual frequency, current products used, flow, dates of previous menstrual cycle, typical cycle length, absorbency of products used, and so forth. Additionally or alternatively, growth data and charts can be used as the wearer's age and/or weight changes significantly. For incontinence products, user-provided information can include incontinence type, current products used, and so forth.

The systems and methods described herein can be used to generate recommendations for a wide variety of absorbent articles, including, for example, products in the feminine hygiene or adult incontinence space. Thus, while many of the figures and examples described herein include a baby for illustrations purposes, this disclosure is not so limited. For products in the feminine hygiene or adult incontinence space, for example, the user of the system can be the subject and an image of the subject can be captured through the use of a camera timer feature or a mirror. The image that is processed in accordance with the present disclosure can include the subject, such as a full body image, or a subject's undergarment lying flat on a flat surface. A scale marker, as described in more detail below, can be the person themselves, if the subject is standing and their entire body is present in the image and a height of the person is provided to the system. Alternately, any other type of scale marker can be included in the image, such as a scale marker that is held in the hand flat against the body, a sticker on the body or clothing, or other suitable object with known dimensions. In some embodiments in which subject takes an image of a reflection in a mirror, the scale marker can be the phone itself, as appearing in the reflection.

Referring now to FIG. 1, a user 122 is depicted interacting with an example disposable article recommendation computing system 100 in accordance with non-limiting embodiment. In FIG. 1, the user 122 is seeking an absorbent article recommendation for a subject 124. The user 122 can position the subject 124 within a field of view 130 of an image capture device 114. In the illustrated embodiment, a scale object 128 is also included in the field of view 130 and captured in an image 118. The size of the scale object 128, or the size of a printed indicia on the scale object 128, can be known to the disposable article recommendation computing system 100. In this regard, the scale object 128 can be, for instance, a standard size sheet of paper, a credit card, a playing card, paper currency, a coin, and so forth. In some embodiments, packages of disposable articles can be sold with a scale object 128. Such a scale object 128 can be printed or otherwise provided on the package or can be an independent object that is contained within the package. In some embodiments, the scale object 128 can be downloaded from a website and printed by the user 122. As described in more detail below, however, in other implementations a scale object 128 is not required to be included in the image 118.

Once the subject 124 is properly positioned within the field of view 130, an image 118 can be collected that includes a representation of the subject 126 and the scale object 128. In some embodiments, aids or guides can be provided to the user 122 to assist with proper alignment and placement of the subject 124 within the field of view 130 of the image capture device 114. The image 118 can be a single image, a plurality of still images, or a movie or video clip of the subject 124.

To ensure the image 118 is usable for the image processing techniques described herein, the disposable article recommendation computing system 100 can execute various routines upon receipt of the image 118. For example, the disposable article recommendation computing system 100 can perform perspective correction in order to account for any keystoning that may be present in the image 118. The amount of correction necessary to account for keystoning may also be determined and the image may be rejected if the correction amount exceeds certain pre-set bounds.

The disposable article recommendation computing system 100 can also perform various error checking routines to ensure the subject 124 is properly oriented and positioned within the field of view 130. Real-time feedback can be provided to the user regarding suggested adjustments, such as positional adjustments or environmental adjustments, which may need to be made before processing can proceed to the next steps. For instance, the subject 124 may need to be lying on their back with the image capture device 114 positioned substantially overhead and an error checking routine can confirm this orientation. Additionally, the scale object 128 may need to be placed so that all four corners, or other attributes of the scale object 128, are visible and properly positioned within the field of view 130. Various error checking routines can also check whether the subject's eyes are open and looking at the image capture device 114, as well as other pose or positional aspects of the subject (i.e., limbs sufficiently visible and properly oriented for analysis). Error checking routines can confirm the subject 128 is properly positioned within the frame, such that the subject 128 is a sufficient distance from the edges of the frame and suitably centered. Various routines can perform, for example, face tracking, pose tracking, object tracking, and so forth. Some initial routines or sub-routines can be performed to increase the overall processing speed of the image analysis and subsequent recommendation. For example, by first running a routine that detects a face of the subject 128, the system can than quickly estimate where the subject's body should be located within the frame. The disposable article recommendation computing system 100 can also confirm that lighting levels are suitable for image processing, confirm the subject is in focus, confirm presence of scale object, and so forth. In the event the image 118 does not satisfy one or more of these checks, or other type of pre-processing check, the user 122 can be requested to provide an additional image 118 in order to correct the issue. Some error checking can be performed, for example, in real-time through execution on the live preview as the subject 124 is being positioned in the field of view 130, either locally or remotely, depending on system configuration. In some embodiments, the user 122 will not be permitted to collect an image with the image capture device 114 until certain criteria are satisfied. Using a live preview, for example, the user can 122 re-position the subject 128 and/or the scale object 128, for example, to satisfy the error checking routines or verification processes.

Figure 2:
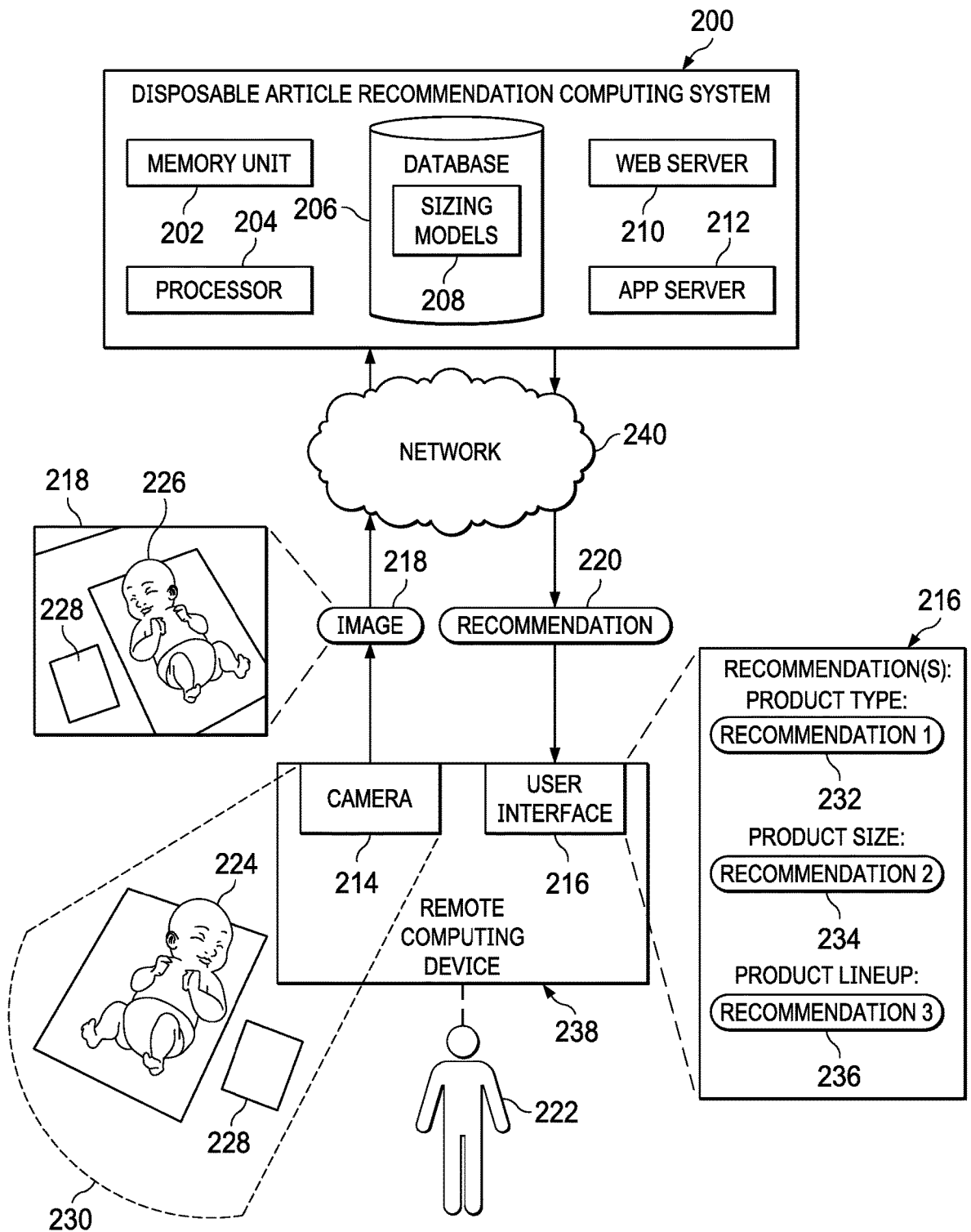
FIG. 2 depicts a user interacting with another example disposable article recommendation computing system.

In some embodiments, certain error checking routines or verification processes can be performed locally at the image capture device 114 (such as, for example, executed by a remote computing device 238 associated with the image capture device 114, shown in FIG. 2) and other process can be performed by the disposable article recommendation computing system 100. For example, one or more routines that can be executed relatively quickly can be executed by a remote computing device. Such high-speed routines may be especially helpful in conjunction with a live-preview screen on the remote computing device, for example, as described in more detail below. Other routines that may require higher levels of accuracy, and potentially more time and resources, can be executed by the disposable article recommendation computing system 100. Further, to increase processing speed, or to match the resolution of images that were used to train various machine-learning models, the image 118 can first be downsampled for initial processing. During initial processing, for example, the corners (or other attributes) of the scale object 128 can be detected using the lower resolution image. As is to be appreciated, various processes associated with the system might optimally run at different resolutions, as is the case with various machine learning algorithms. Further, some processes may run too slowly on a full resolution image. In some embodiments, after each algorithm runs at its optimal resolution, the data can be re-mapped to the original image resolution (or a single downsampled resolution, for example). Various combinations of up-sampling, down-sampling, cropping, or using parts of the image may be used. Downsampling can also decrease file sizes which can beneficially allow downsampled images to be sent between various devices more quickly than full resolution images. Once a suitable image 118 is collected and corrected for perspective, the disposable article recommendation computing system 100 can determine a scale for the image 118. While the scale of the image 118 can be determined using a variety of suitable techniques, the scale of the image 118 in FIG. 1 can be determined based on the known dimensions of the scale object 128. For instance, with the knowledge that the scale object 128 is an 8.5" by 11" sheet of paper, the disposable article recommendation computing system 100 can determine the overall scale of the image 118. Thus, a pixels to inches conversion, or other suitable scale, can be determined for the image 118 by the disposable article recommendation computing system 100.

The disposable article recommendation computing system 100 can perform various processing to identify physical attributes of the subject 124, as represented in the image 118. In some embodiments, for example, joint locations, such as ankles, hips, shoulders, and so forth, are identified. Using the scale of the image 118, the disposable article recommendation computing system 100 can then determine various dimensions of the physical attributes of the subject 124. As provided herein, any of a variety of techniques can be used to determine the various dimensions of the physical attributes, such as linear correlation models, machine learning algorithms, and so forth. Non-limiting examples of dimensions that can be determined include, without limitation, hip width, waist width, torso length, distance between ears, distance between pupils, and so forth.

Once the physical attributes of the subject 124 are determined, a plurality of fit parameters can be generated. The fit parameters can correlate to one or more parameters used to generate sizing models for various absorbent articles. In FIG. 1, the fit parameters generated by the disposable article recommendation computing system 100 comprise an estimated waist circumference of the subject 124, an estimated thigh circumference of the subject 124, and an estimated rise measurement of the subject 124. As is to be appreciated however, any of a variety of different types of fit parameters can be utilized.

A plurality of sizing models 108 for pre-made absorbent articles can be stored within a database 106. Generally, each pre-made absorbent article can have an associated sizing model 108 that includes fit parameter ranges for that particular article. In the illustrated embodiment, for example, each sizing model 108 is a three-dimensional model that includes a range of waist circumferences, a range of thigh circumferences, and a range of rise measurements associated with a particular absorbent article. In other embodiments, the sizing models can utilize different fit parameters. Upon determination of the fit parameters for the subject 124, the disposable article recommendation computing system 100 can apply the fit parameters to the sizing models 108 to determine which pre-made disposable article is appropriately sized for the subject 124. In some instances, the fit parameters for the subject 124 may fall within the bounds of multiple different sizing models 108 that are each associated with different sizes of absorbent articles. In such cases, the disposable article recommendation computing system 100 can make a recommendation based on which absorbent article is likely to fit better. In some configurations, however, the fit parameters or other physical attributes of the wearer, can be utilized to manufacture custom-made absorbent articles in an on-demand manufacturing process. For instance, custom-made absorbent articles may have a certain base design, while allowing for certain aspects to be modified and custom configured to fit an intended subject, based on the fit parameters for the subject. Subsequent to manufacturing the custom-made absorbent article, the absorbent articles can be direct shipped to the subject's household or shipped to a retail location proximate to the subject, for example.

Referring still to FIG. 1, a recommendation 120 can be provided to the user 122 via a suitable user interface 116. The user interface 116 can be any suitable device or method capable of communicating information to the user 122, such as the display screen of a computing device, a text message, an email message, an in-app message, and so forth. The scope of the recommendation 120 can vary. In some implementations, the recommendation 120 identifies a size of absorbent article that is suitable for the subject 124, shown as product size recommendation 134. In some implementations, the recommendation 120 can include additional information, such as a product type recommendation 132 and a product lineup recommendation 136. This additional information can provide recommendations regarding whether the subject 124 should wear a taped-diaper or a training pant diaper, for example. Further, the recommendation 120 can indicate a recommended number of products of a particular size to purchase (i.e., based on the expected growth of the subject 124). The recommendation 120 can also indicate when a product size-up will be recommended. Depending on the type of product, the recommendation 120 may indicate the size of a disposable liner or disposable insert, for example. The recommendation 120 can also provide purchase information, such as identifying an online or brick-and-mortar retailer selling the recommended product, and/or provide information regarding a subscription purchase program. Generally, a subscription purchase program can routinely send the user 122 batches of the recommended size of the disposable articles over time. In some cases, the size of the disposable articles provided in the batches can be automatically increased over time to account for the growth of the subject 124.

The disposable article recommendation computing system 100 can be provided using any suitable processor-based device or system, such as a personal computer, mobile communication device, laptop, tablet, server, mainframe, or a collection (e.g., network) of multiple computers, for example. The disposable article recommendation computing system 100 can include one or more processors 104 and one or more computer memory units 102. For convenience, only one processor 104 and only one memory unit 102 are shown in FIG. 1. The processor 104 can execute software instructions stored on the memory unit 102. The processor 104 can be implemented as an integrated circuit (IC) having one or multiple cores. The disposable article recommendation computing system 100 can also utilize one or more Graphical Processing Units (GPU) to assist with various aspects of image processing, such as to execute one or more machine learning models and/or convolutional neural network models that are applicable for visual imagery analysis. The memory unit 102 can include volatile and/or non-volatile memory units. Volatile memory units can include random access memory (RAM), for example. Non-volatile memory units can include read only memory (ROM), for example, as well as mechanical non-volatile memory systems, such as, for example, a hard disk drive, an optical disk drive, etc. The RAM and/or ROM memory units can be implemented as discrete memory ICs, for example.

The memory unit 102 can store executable software and data for use by the disposable article recommendation computing system 100 described herein. When the processor 104 of the disposable article recommendation computing system 100 executes the software, the processor 104 can be caused to perform the various operations of the disposable article recommendation computing system 100, such as analyze images, determine physical attributes and fit parameters, compare fit parameters to sizing models, and provide recommendations to users.

Data used by disposable article recommendation computing system 100 can be from various sources, such as the database(s) 106, which can be electronic computer databases, for example. The data stored in the database(s) 106 can be stored in a non-volatile computer memory, such as a hard disk drive, a read only memory (e.g., a ROM IC), or other types of non-volatile memory. In some embodiments, one or more databases 106 can be stored on a remote electronic computer system, for example. As it to be appreciated, a variety of other databases, or other types of memory storage structures, can be utilized or otherwise associated with the disposable article recommendation computing system 100.

In accordance with various embodiments, the disposable article recommendation computing system 100 can include one or more computer servers, which can include one or more web servers, one or more application servers, and/or one or more other types of servers. For convenience, only one web server 110 and one application server 112 are depicted in FIG. 1, although one having ordinary skill in the art would appreciate that the disclosure is not so limited. The servers 110, 112 can be comprised of processors (e.g. CPUs), memory units (e.g. RAM, ROM), non-volatile storage systems (e.g. hard disk drive systems), and other elements.

In some embodiments, the web server 110 can provide a graphical web user interface, such as the user interface 116, through which various users 122 can interact with the disposable article recommendation computing system 100. The graphical web user interface can also be referred to as a client portal, client interface, graphical client interface, and so forth. The web server 110 can accept requests, such as HTTP/HTTPS requests, from various entities, such as HTTP/HTTPS responses, along with optional data content, such as web pages (e.g. HTML documents) and linked objects (such as images, video, and so forth). The application server 112 can provide a user interface, such as the interface 116, for users who do not communicate with the disposable article recommendation computing system 100 using a web browser. Such users can have special software installed on their computing devices to allow the user to communicate with the application server 112 via a communication network, as described in more detail below. Further the user interface may comprise a connection to an automated or human agent through any suitable communication portal, such as chat, voice, or video, to walk the user through the use of the recommendation computing system.

The user 122 can be presented with the interface 116, as generated by the disposable article recommendation computing system 100. The user 122 can utilize, for example, a mobile phone, a smartphone, a tablet, a laptop, a desktop, a kiosk, or other computing device capable of displaying the interface 116. As provided above, the interface 116 can identify one or more recommendations 120 based on the image analysis and processing above.

An alternative embodiment of a disposable article recommendation computing system 200 is illustrated in FIG. 2 and can be similar to, or the same in many respects as, the disposable article recommendation computing system 100 illustrated in FIG. 1. For example, the disposable article recommendation computing system 200 can include a memory unit 202, processor 204, and a database 206 for storing sizing models 208. The disposable article recommendation computing system 100 can comprise various software programs such as system programs and applications to provide computing capabilities in accordance with the described embodiments. System programs can include, without limitation, an operating system (OS), device drivers, programming tools, utility programs, software libraries, application programming interfaces (APIs), and so forth. Exemplary operating systems can include local operating systems as well as utilize cloud-based computing services, such as MICROSOFT AZURE SERVER, AMAZON WEB SERVICES (AWS), ALIBABA CLOUD, among others.

The disposable article recommendation computing system 200 can also include various servers, such as a web server 210 and or an app server 212. As shown in FIG. 2, a user 222 can interact with the disposable article recommendation computing system 200 via a remote computing device 238 having a camera 214 and a user interface 216. The remote computing device 238, can be any type computer device suitable for communication over the network, such as a wearable computing device, a mobile telephone, a tablet computer, a device that is a combination handheld computer and mobile telephone (sometimes referred to as a "smart phone"), a personal computer (such as a laptop computer, netbook computer, desktop computer, and so forth), or any other suitable networked communications device, such as personal digital assistants (PDA), mobile gaming devices, or media players, for example.

The remote computing device 238 can, in some embodiments, provide a variety of applications for allowing the user 222 to accomplish one or more specific tasks using the disposable article recommendation computing system 200. Applications can include, without limitation, a web browser application (e.g., INTERNET EXPLORER, MOZILLA, FIREFOX, SAFARI, OPERA, NETSCAPE NAVIGATOR) telephone application (e.g., cellular, VoIP, PTT), networking application, messaging application (e.g., e-mail, IM, SMS, MMS, BLACKBERRY Messenger, WeChat, XiaoHongShu, WhatsApp), and so forth. The remote computing device 238 can comprise various software programs such as system programs and applications to provide computing capabilities in accordance with the described embodiments. System programs can include, without limitation, an operating system (OS), device drivers, programming tools, utility programs, software libraries, application programming interfaces (APIs), and so forth. Exemplary operating systems can include, for example and without limitation, a PALM OS, MICROSOFT OS, APPLE OS, ANDROID OS, UNIX OS, LINUX OS, SYMBIAN OS, EMBEDIX OS, Binary Runtime Environment for Wireless (BREW) OS, JavaOS, a Wireless Application Protocol (WAP) OS, as well as cloud-based computing services, such as MICROSOFT AZURE SERVER, AMAZON WEB SERVICES (AWS), ALIBABA CLOUD, among others.

The remote computing device 238 can include various components for interacting with the disposable article recommendation computing system 200. The remote computing device 238 can include components for use with one or more applications such as a stylus, a touch-sensitive screen, keys (e.g., input keys, preset and programmable hot keys), buttons (e.g., action buttons, a multidirectional navigation button, preset and programmable shortcut buttons), switches, a microphone, speakers, an audio headset, depth sensor, IR projector, stereoscopic cameras, gyroscope, accelerometer, and so forth. The user 222 can interact with the disposable article recommendation computing system 200 via a variety of other electronic communications techniques, such as, without limitation, HTTP requests, in-app messaging, and short message service (SMS) messages. The electronic communications can be generated by a specialized application executed on the remote computing device 238 or can be generated using one or more applications that are generally standard to the remote computing device 238. The applications can be included or be implemented as executable computer program instructions stored on computer-readable storage media such as volatile or non-volatile memory capable of being retrieved and executed by a processor to provide operations for the remote computing device 238. The memory can also store various databases and/or other types of data structures (e.g., arrays, files, tables, records) for storing data for use by the processor and/or other elements of the remote computing device 238.

Similar to the process depicted in FIG. 1, the user 222 can collect an image 218 of a subject 224 by placing the subject 224 in the field of view 230 of the camera 214. In the context of a mobile phone, for example, the camera 214 can be a rear-facing camera that provides a preview of the image on the user interface 216. As shown, a scale object 228 can be included in the image 218 for image processing by the disposable article recommendation computing system 200. In the illustrated embodiment, the image 218, including a representation of the subject 226, is provided to the disposable article recommendation computing system 200 via an electronic communications network 240. The communications network can include a number of computer and/or data networks, including the Internet, LANs, WANs, GPRS networks, LTE networks, etc., and can comprise wired and/or wireless communication links. In some embodiments, prior to providing the image 218 to the disposable article recommendation computing system 200, the remote computing device 238 can perform various types of pre-processing, such as an error checking routine. Further, as described in more detail below with regard to FIGS. 3-6, in some embodiments, the remote computing device 238 can perform image processing on the image 218 and provide the output of the image processing to the disposable article recommendation computing system 200.

Still referring to FIG. 2, upon receipt of the image 218, the disposable article recommendation computing system 200 can perform processing as described in FIG. 1 in order to generate a recommendation 220 for the user 222. The recommendation 220 can then be sent via the network 240 for display on the user interface 216 of the remote computing device 238. The scope, format, and content of the recommendation 220 can vary. In the illustrated embodiment, the recommendation 220 includes a recommended product type 232, a recommended produce size 234, and a recommended product lineup 236, although this disclosure is not so limited.

Figure 3A:
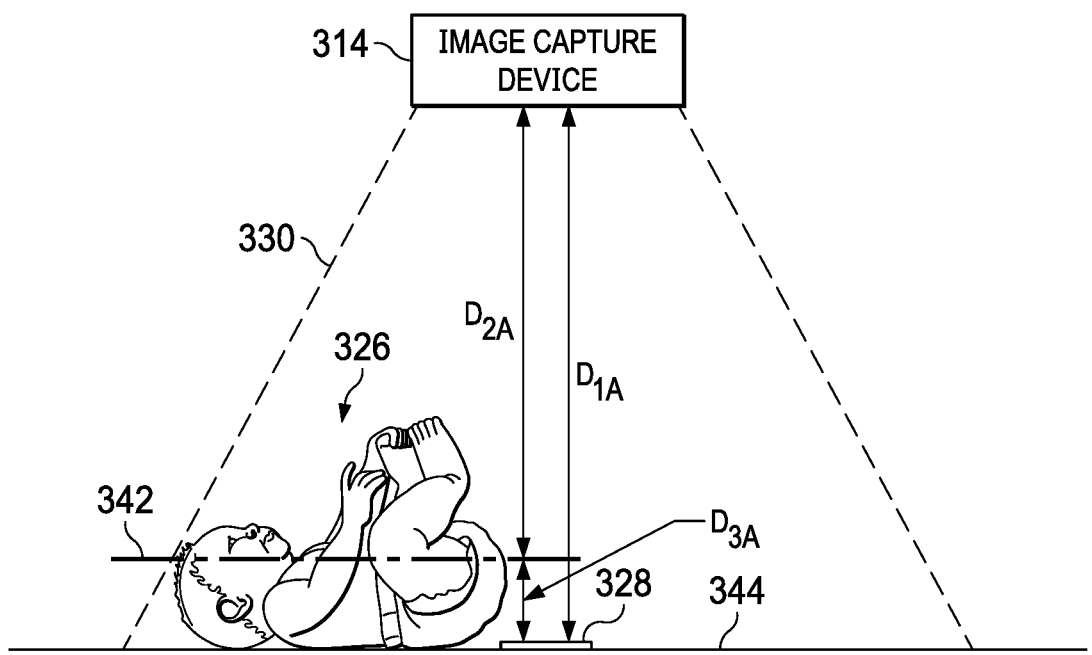
FIGS. 3A-3C depict an example scale object and a subject placed within the field of view of an image capture device.
Figure 3C:
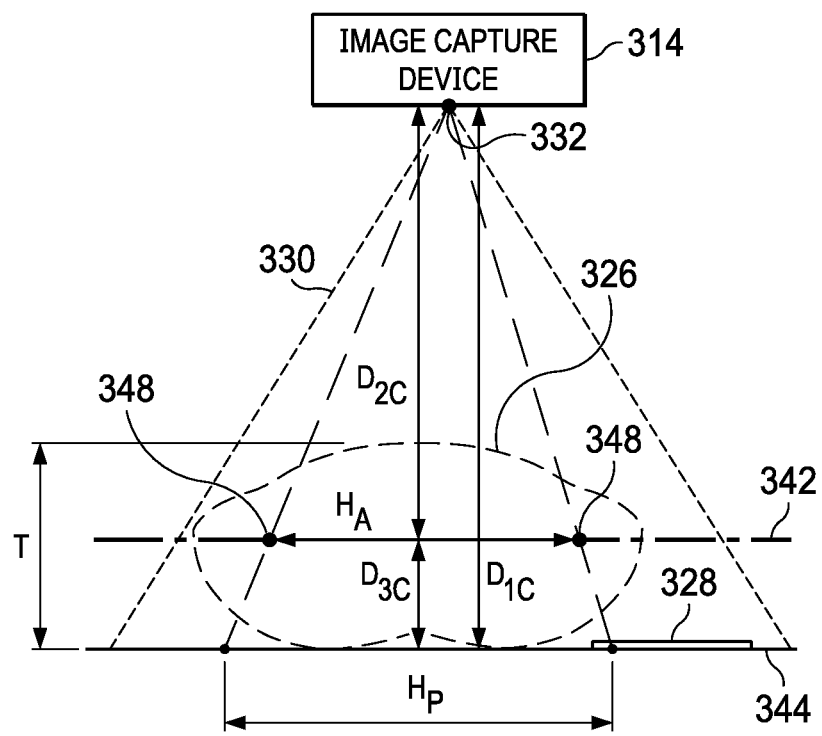
Figure 3B:
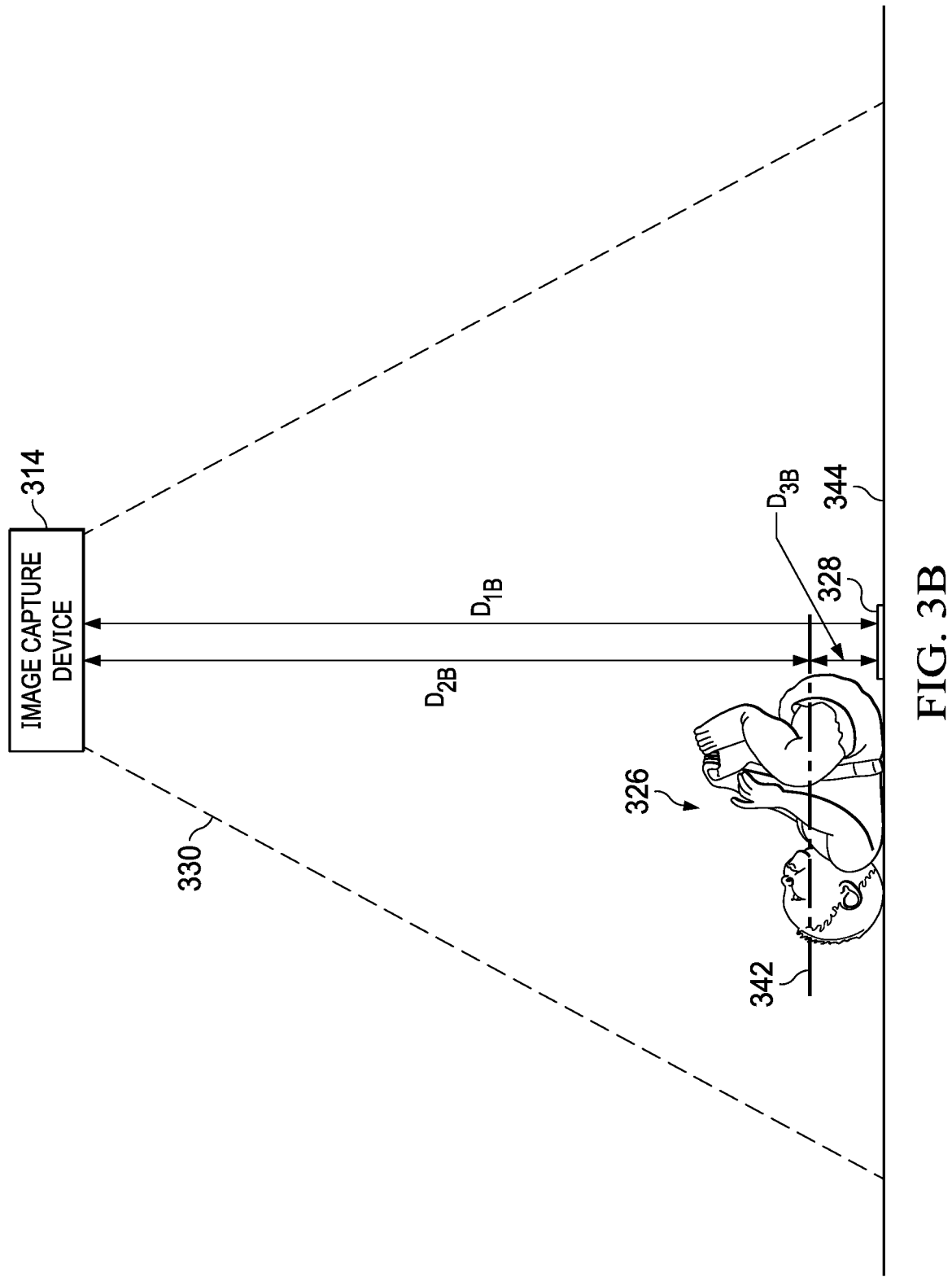

Referring now to FIGS. 3A-3B, side views of an example scale object 328 and a subject 326 each positioned proximate to an image capture device 314 having a field of view 330 are shown. In both FIGS. 3A-3B, the scale object 328 is shown placed on the same plane upon which the subject 326 is laying, which is referred to herein as a scale object focal plane 344. The scale object focal plane 344 can be generally co-planar with, for example, a floor, a bed, a crib, or other surface upon which the subject 326 is placed. Due to the volume of the subject 326, the hips of the subject 326 are not co-planar with the scale object focal plane 344. Instead, the hips of the subject 326 lay in a hip focal plane 342, which is generally parallel to the scale object focal plane 344, but in closer proximity to the image capture device 314 than the scale object focal plane 344.

Determining a scale of an image collected by the image capture device 314 based on the scale object 328 determines the scale of objects that are co-planar with the scale object focal plane 344. Therefore, depending on the distance between the subject 326 and the image capture device 314, this scale may not provide sufficient accuracy for determining the scale for the hip focal plane 342. In accordance with various embodiments of the present disclosure, however, the distance between the scale object focal plane 344 and the hip focal plane 342 can be calculated, estimated, or measured and then used to determine the scale of the hip focal plane 342, thus allowing for more accurate determination of the dimensions of the subject 326 through image analysis. It is noted, however, that in accordance with other embodiments, the sizing recommendation processes described herein can be based on the scale of the scale object focal plane 344, without accounting for any potential difference in scale between the scale object focal plane 344 and the focal plane(s) in which the physical attributes of the subject may lie.

The difference between the scale of the hip focal plane 342 and the scale object focal plane 344 will decrease as the image capture device 314 is pulled further away from the subject 326. In FIG. 3A the image capture device 314 is relatively close to the subject 336, with the distance between the image capture device 314 and the scale object focal plane 344 shown as distance $D_{1A}$ and the distance between the image capture device 314 and the hip focal plane 342 shown as distance $D_{2A}$. The distance between the hip focal plane 342 and the scale object focal plane 344 is shown as distance $D_{3A}$, which is equivalent to $D_{1A}$ minus $D_{2A}$. In FIG. 3B, the image capture device 314 is positioned further away and the distance between the image capture device 314 and the scale object focal plane 344 is shown as distance $D_{1B}$ and the distance between the image capture device 314 and the hip focal plane 342 is shown as distance $D_{2B}$. The distance between the hip focal plane 342 and the scale object focal plane 344 is shown as distance $D_{3B}$, which is equivalent to $D_{1B}$ minus $D_{2B}$. As the image capture device 314 is pulled away from the subject 326 (i.e., moves from the position shown in FIG. 3A to the position shown in FIG. 3B), the distance $D_3$ becomes a smaller portion of the distance $D_1$ and the difference in scale of the hip focal plane 342 and the scale object focal plane 344 decreases. Accordingly, if the image capture device 314 is positioned at a sufficient distance away from the subject 326, the difference in scale between the scale object 328 and the subject 326 does not substantially impact the size recommendations and can be considered negligible. However, in situations where the differences in scale are non-negligible, the image processing described herein can take into consideration the distance between the hip focal plane 342 and the scale object focal plane 344 and compensate for the difference, thereby avoiding a situation where the calculated dimensions of the subject 326 are determined to be larger than the actual physical dimensions.

A variety of suitable techniques can be used to compensate for the differences between the scale of the hip focal plane 342 (as determined through the scale object 328) and the scale object focal plane 344. It is noted, however, that some embodiments of the present disclosure do not seek to compensate for any difference between the scale of the hip focal plane 342 and the scale object focal plane 344, irrespective of the magnitude of the difference. Should it be desired to compensate for the difference in scale, the difference in the scale of the hip focal plane 342 to the scale object focal plane 344 is linearly proportional to the distance between the hip focal plane 342 and scale object focal plane 344 to the nodal point 332 (FIG. 3C) of the image capture device 314. As understood in the art, the nodal point is the point in which all rays entering the lens of the image capture device 324 converge. Further, the focal length provides the distance between the nodal point and the image sensor of the image capture device 314. The focal length of the image capture device 314 can be provided in metadata in the captured image. Using the focal length of the image capture device 314, the projected size of the subject 326 as if it were co-planar with the scale object focal plane 344, and the distance between the scale object focal plane 344 and the hip focal plane 342, the scale of the hip focal plane 342 can be determined.

Referring now to FIG. 3C, a cross sectional end view of a torso of the subject 326 with the hips 348 schematically shown. The hips 348 lie in the hip focal plane 342. The distance $D_{1C}$ can be determined based on the pixel size of the image on image capture device 314 and the focal length of the image capture device 314 (as provided in the image metadata), as the size of the scale object 328 is known (i.e., 8½" by 11", or other suitable size). In some embodiments, if the distance $D_{1C}$ is deemed to exceed a certain threshold, the dimensions of subject 326 can be determined without any adjustment for the separation of the scale object focal plane 344 and the hip focal plane 342. However, in some embodiments, further processing can be performed to provide such an adjustment in order to more accurately determine various dimensions of the subject 326. In one embodiment, the actual hip width (i.e., dimension $H_A$ in FIG. 3C) can be derived based on the pixel size of the subject's projected hip width $H_P$ on the scale object focal plane 344 dimension, as collected by the image capture device 324 and the distance $D_{1C}$. For example, a hip plane constant can be used to determine how far the hip focal plane 342 is above the scale object focal plane 344 based on the projected hip width $H_P$ on the scale object focal plane 344 of the subject 326, shown as distance $D_{3C}$. In one example implementation, the thickness T of a subject 326 is deemed to be about 90% the hip dimension $H_A$ of the subject. Further, the hips of the subject are deemed to lie in the middle of the subject's height in a side view (i.e., 50% of the thickness T). Thus, the subject's hips may lay in a plane that is about 0.45 times the hip width above the scale object focal plane 344, with the hip plane constant of 0.45 calculated as the product of 0.9 and 0.5. As such, distance $D_{3C}$ can be estimated as 0.45 times the hip dimension $H_A$. Once the distance $D_{3C}$ is determined, the scale of the hip focal plane 342 can be linearly extrapolated from the scale of the scale object focal plane 344, as determined based on the scale object 328. It is to be appreciated, that while a hip plane constant of 0.45 is provided herein, other hip plane constants can be used without departing from the scope of the present disclosure.

Figure 4:
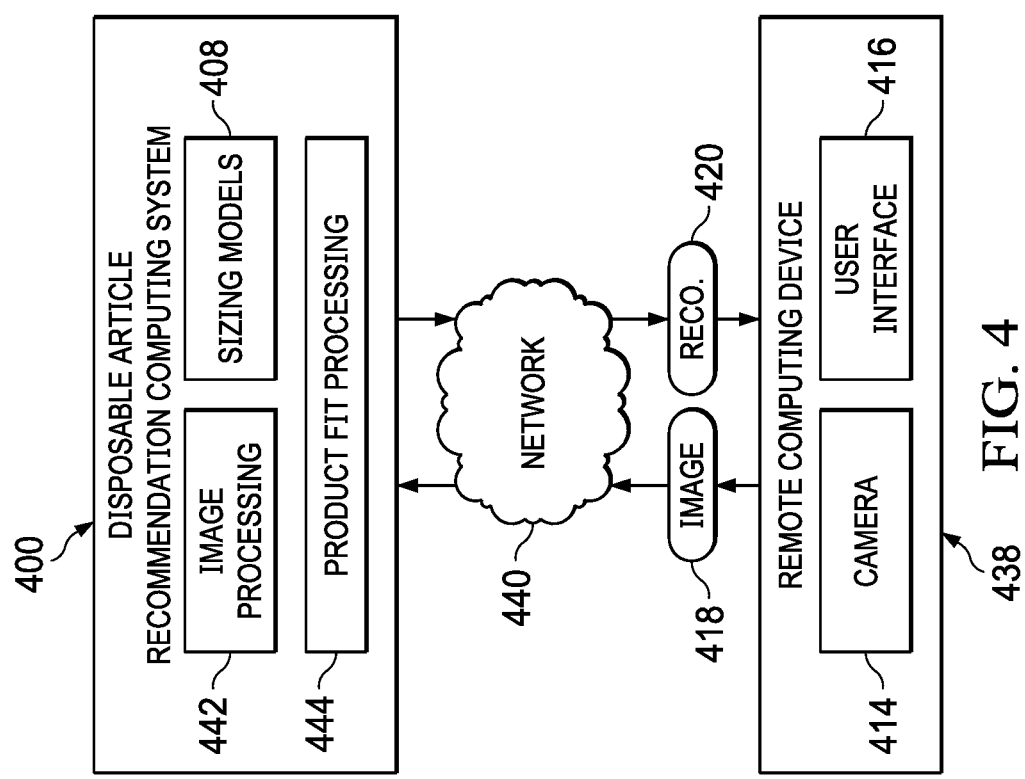

Moreover, in accordance with various implementations, other approaches can be used to measure the distance between the hip focal plane 342 and the scale object focal plane 344. For example, the distance to the hip focal plane 342 and the scale object focal plane 344 can be directly measured by an instrument associated with image capture device 314. Such distances can be measured, or at least interpolated, by stereophotogrammetry, infrared triangulation, laser range finding, infrared time-of-flight, or combinations thereof. In some implementations multiple images taken simultaneously at multiple positions can be analyzed, such as when a remote computing device has multiple image capture devices 314. In any event, any of a variety of approaches can be used in accordance with the systems and methods described herein to accurately account for vertical differences between the plane in which the scale object 328 is placed and the plane(s) of physical features of the subject 326. FIGS. 4-7 schematically depict various example operational arrangements for disposable article recommendation computing systems in accordance with the present disclosure. Referring first to FIG. 4, an operational arrangement similar to that depicted in FIG. 2 is shown. Namely, a remote computing device 438 collects an image 418 using a camera 414. The image 418 is provided to a disposable article recommendation computing system 400 via an electronic communications network 440. The disposable article recommendation computing system 400 is configured to perform image processing 442 to determine the fit parameters for a subject in the image 418. The disposable article recommendation computing system 400 is further configured to perform product fit processing 444 to apply the fit parameters for the subject in the image 418 to sizing models 408. Subsequent to the image processing 442 and the product fit processing 444, the disposable article recommendation computing system 400 can transmit a recommendation 420 to display on a user interface 416 of the remote computing device 438.

Figure 5:
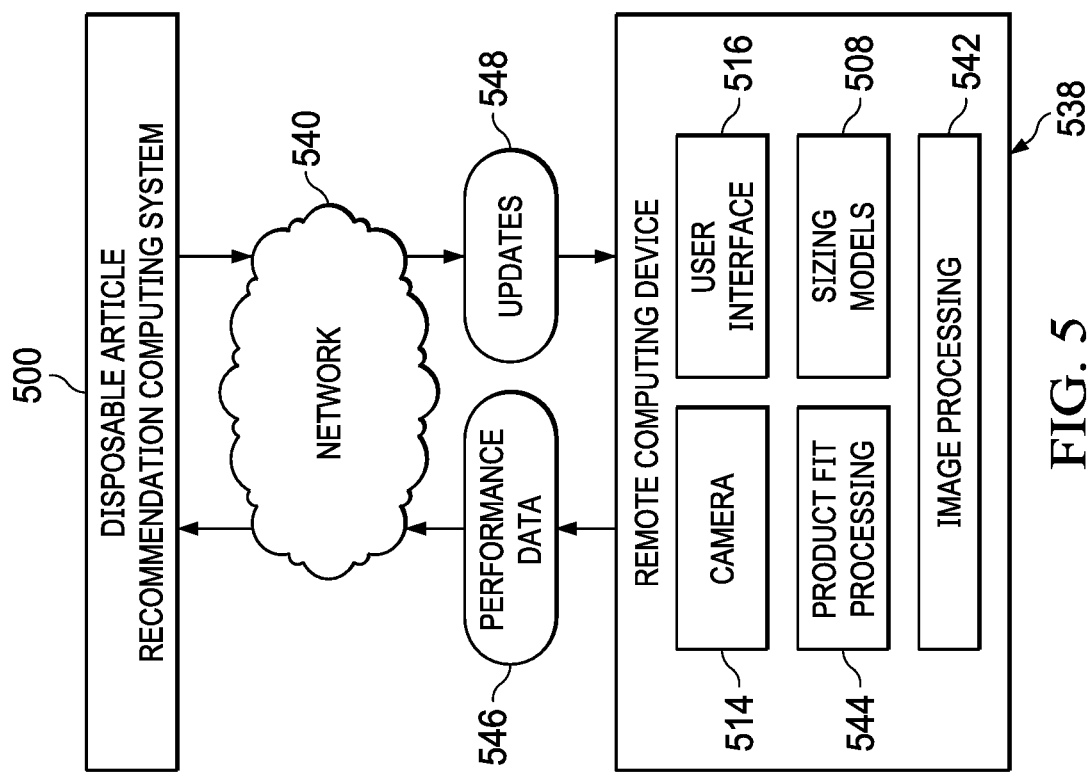
FIGS. 4-7 depict various example operational arrangements for disposable article recommendation computing systems.
Figure 6:
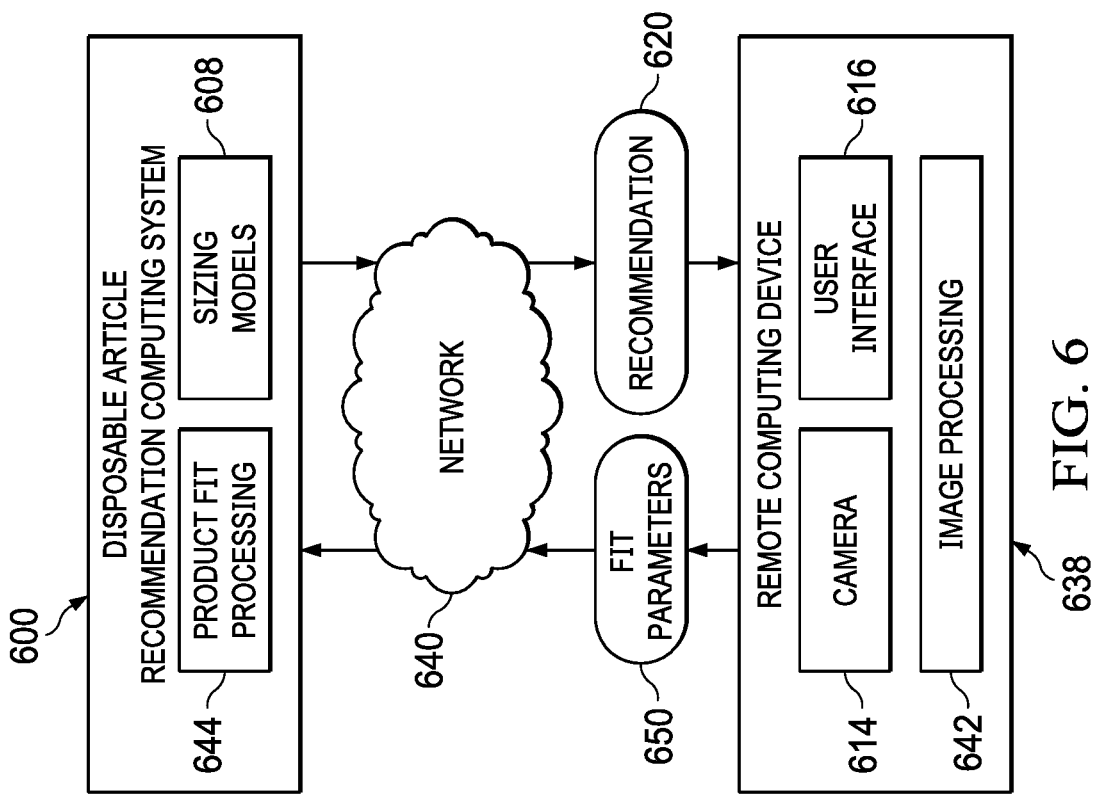

FIG. 5 depicts an embodiment with an alternative operational arrangement. As shown, a remote computing device 538 includes a camera 514 and a user interface 516, similar to previously described embodiments. In this embodiment, however, sizing models 508 are stored by the remote computing device 538. Also, image processing 542 and product fit processing 544 are performed by the remote computing device 538. As such, the remote computing device 538 can generally offer the functionality of the disposable article recommendation computing system 100, for example. As shown, in some embodiments, the remote computing device 538 can provide various data to a disposable article recommendation computing system 500 through a network 540. In the illustrated embodiment, performance data 546 is provided to the disposable article recommendation computing system 500 and various updates 548 can be provided to the remote computing device 538. Performance data 546 can be collected from a user of the remote computing device 538 and can relate to, for example, the quality of the absorbent article recommendation based on the product fit or product performance. The performance data 546, as collected from a multitude of users, can be useful in altering and updating various fit parameters over time, such as using a self-learning model. Such updated fit parameters can then be provided to the remote computing device 538 in an effort to continually improve the product fit recommendations over time. FIG. 6 depicts yet another example alternative operational arrangement. In this embodiments, a remote computing device 638 has a camera 614 and a user interface 616. The remote computing device 638 is configured to perform image processing 642 on the image collected by the camera 614. As a result of this image processing 642, fit parameters 650 can be determined and provided to a disposable article recommendation computing system 600 via communications through a communication network 640. Upon receipt of the fit parameters 650, the disposable article recommendation computing system 600 can execute product fit processing 644 to apply the received fit parameters 650 to sizing models 608. The disposable article recommendation computing system 600 can then provide a recommendation 620 to the remote computing device 638 for display on the user interface 616. Thus, FIG. 6 depicts an example operational arrangement in which the processing steps are split between the remote computing device 638 and the disposable article recommendation computing system 600.

Figure 7:
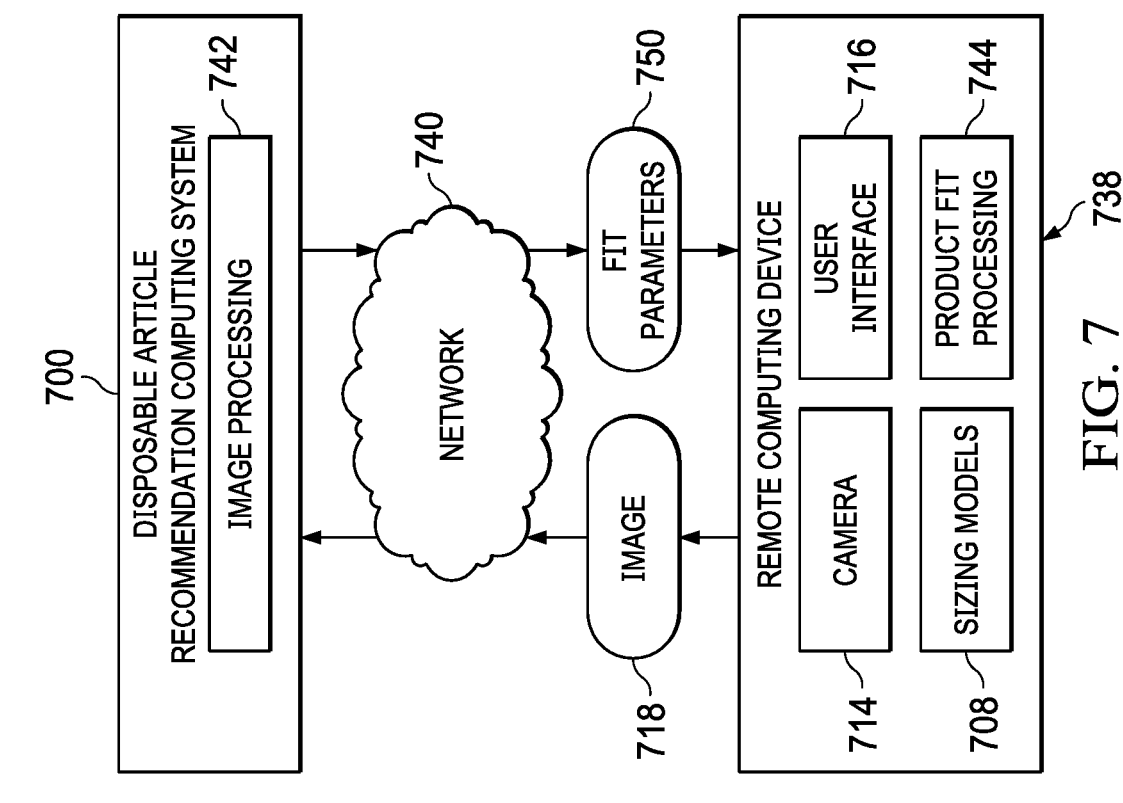

FIG. 7 depicts another embodiment with an alternative operational arrangement that splits processing between a remote computing device and a disposable article recommendation computing system. In this example arrangement, sizing models 708 are stored by the remote computing device 738. A camera 714 of the remote computing device is used to collect an image 718 that is provided to a disposable article recommendation computing system 700 through a communications network 740. The disposable article recommendation computing system 700 is configured to perform imaging processing 742 in order to determine fit parameters 750. The fit parameters 750 can then be communicated to the remote computing device 738 for product fit processing 744. The product fit processing 744 can apply the fit parameters 750 to the sizing models 708 and generate a recommendation for display on a user interface 716.

As shown in FIGS. 3-6, some processing may occur locally on the remote computing device while other processing may occur at the disposable article recommendation computing system. As such, relatively fast algorithms that can be executed on the remote computing device can be separated from relatively slow algorithms that that are performed on the server-side. This approach can allow for real-time live preview guidance to the user, for example, as such routines supporting real-time live preview guidance functionality can be executed locally by the remote computing device. Accordingly, with regard to identifying the scale object and determining the scale of the image, a combination of processes can be used, which includes low resolution object detection algorithms that first determine the region of the image where the scale object is located. Such processes can be executed locally at the remote computing device, for example. Such processes may further include high resolution object detection algorithms that seek to identify optimal search neighborhoods for particular features of the scale object, such as a corner, an edge, printed indicia, and so forth. The high resolution algorithms or processes may run on the disposable article recommendation computing system. The processes may further include various refinement algorithms, such as edge detection algorithms, to precisely locate a feature of the scale object. These algorithms may be combined in various ways, including feeding a partial image from one algorithm to the next (i.e., directed search), weighting an algorithm's search parameters based on the input of another algorithm, or selecting the result of a single algorithm based on the confidence with which it located the feature of interest.

Thus, in some embodiments, a set of ultra-low resolution algorithms can run on the remote computing device. More particularly, these algorithms can be fast enough to execute on a remote computing device while sufficiently providing enough guidance and/or error checking. These algorithms may not necessarily be accurate enough to determine a subject's body dimensions, however. A goal of these algorithms is to provide additional error checking while also providing guidance to the high resolution algorithm. High resolution algorithms executed by the disposable article recommendation computing system, for example, can precisely select points of interest in the image, with the search guided by low resolution results. In some cases, this high resolution algorithm is the algorithm that can be precise enough to use as the basis for the models.

For illustration purposes only, below provides an example interplay of various processes in accordance with one non-limiting embodiment. First, a suitable programming function can be executed by the remote computing device to locate a scale object. In some embodiments an open source computing vision library, such as OpenCV, can be used for this process. This process can be used to guide the user to place the scale object in the proper location in the frame, error check for the presence of the scale object, and so forth. This process can use simple object detection, for example, to put a bounding box around the scale object, although this process is not necessarily designed to find the edges or corners or perform image segmentation. Next, at the disposable article recommendation computing system, a first pass with a machine learning algorithm can confirm that an un-wrinkled white piece of paper or other suitable scale object is present (i.e., error check) and locates search neighborhoods for the corners or other attributes, as may be the case. An edge detection algorithm can then be executed by the disposable article recommendation computing system within the corner search neighborhoods to precisely select the scale object corners, or other attributes. It is noted that various edges appear throughout the image, which is why it is beneficial that this algorithm is focused on the particular area where the scale object appears. Once identified, these locations can then be used for scaling the image in accordance with the present disclosure.

Figure 8:
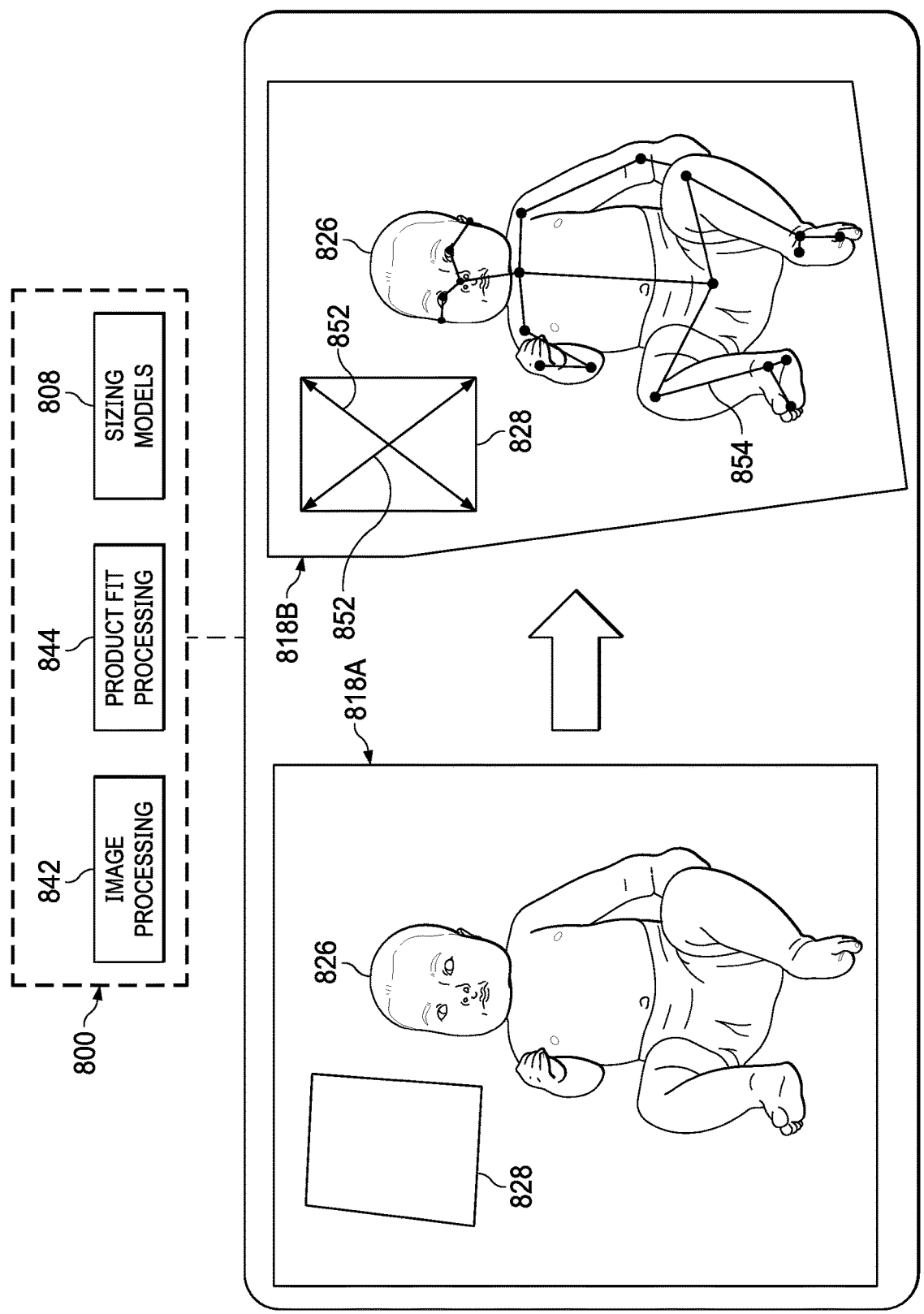
FIG. 8 depicts example processing that can be performed by a disposable article recommendation computing system.

In any event, by sharing the various image processing algorithms between the local remote computing device and the disposable article recommendation computing system, the overall accuracy and speed of the size recommendation process can be optimized while also allowing for scalability across a large number of simultaneous users. Referring now to FIG. 8, example processing that can be performed by a disposable article recommendation computing system 800 is schematically illustrated. The disposable article recommendation computing system 800 can receive an unprocessed image 818A that includes a representation of a subject 826 and a scale object 828. During image processing 842, a variety of error checks can be performed on the unprocessed image 818A to ensure the image is suitable for analysis. The image processing 842 can also correct for any keystone effect, which is distortion caused by the relative angle between the image capture device and the subject. Any suitable approach for keystone correction can be utilized, including leveraging information collected by sensors associated with the camera, such as accelerometers, gyroscope, and so forth, to assist in the correcting for the camera's angle. Image processing 842 may make any other image corrections that may be needed, such as corrections or adjustments to light, color, intrinsic camera parameters, lens distortion, or other distortion, for example. Further, the amount of corrections needed to the image may be quantified for an image such that if corrections are required beyond a threshold value that would impact accuracy of the recommendation, a new image is requested.

With specific regard to performing image processing routines on the scale object, in accordance with various embodiments, a variety of error checking routines can be executed to ensure the scale object included in the image is sufficient and usable by the system. For example, confidence levels on aspects of the scale object identification may be used. In some embodiments, a confidence level of the corner detection of a sheet of paper or the edge of a paper is ascertained to determine whether the scale object in the image is acceptable. Additionally or alternatively, various algorithms can be used to determine whether an appropriate scale object is present and search for other factors besides edges or corners of the scale object, for example. In one implementation, image analysis is performed to determine if the scale object includes print or lines in an attempt to determine if the scale object is actually appropriate for processing. The image analysis can also detect for whether holes are present in the scale object (such as 3 ring binder holes, or spiral binder holes). The image analysis can also check, for example, whether a corner may not be visible due to tearing or look for evidence of folding or bending of the scale object. It can be determined if the scale object is unusable and request another image with a suitable scale object, or, in some cases, not allow for an image to be collected until the issues with the scale object are addressed. Additionally, algorithms in accordance with the present disclosure may search for the linearity of an edge or otherwise fit the scale object to an anticipated shape (for example, a rectangle, or a circle) to determine if the scale object has been folded or otherwise deformed. Algorithms may also search for texture to detect wrinkles in the surface of the scale object. Based on the outcome of the algorithms pertaining to the scale object, the system can determine whether to continue processing the remaining image or reject the image and request a different image from the user. In some embodiments, a notification can be provided to the user regarding the reasoning for the rejection (i.e., missing corner, wrinkles detected, incorrect aspect ratio, etc.). Beyond the error checking and verification routines associated with the scale object, a variety of similar routines can be executed with regard to the analysis of the subject. For instance, in some embodiments, a confidence value for each joint position and/or the number of joint positions predicted for a single joint may be used to detect errors and to determine if the image is suitable for use. Thus, in accordance with the systems and method described herein, a wide variety of error checking can be performed at various points during processing to ensure the image is suitable for use.

Subsequent to correcting for any keystone effect, among any other issues, and satisfying any other error checks, the processed image 818B can be analyzed to determine its scale. In some embodiments, detected scale attributes 852 of the scale object 828 are utilized to determine the scale of the processed image 818B. For instance, if the scale object 828 is a conventional sheet of paper with measurement of 8.5 inches by 11 inches, the disposable article recommendation computing system 800 can identify the scale object 828 and then measure the corner to corner dimensions of the scale object 828 during imaging processing 842. The disposable article recommendation computing system 800 can also confirm that both of the corner to corner dimensions are similar, which confirms the correction for any keystone effect was successful. Then, based on the known corner to corner dimension of 13.9 inches for the sheet of paper, the disposable article recommendation computing system 800 can determine the scale for the processed image 818B. In some embodiments, analyzing the aspect ratio of the scale object 828 before and/or after correction, or similarly any dimension of the scale object (e.g. first side length, second side length, width, diagonal, etc.) before and/or after correction, may be used to detect images that are not suitable for processing a recommendation. In some embodiments, the unprocessed image 818A can include more than one scale object 828 such that one of the scale objects in the image is used for perspective correction, the other scale object(s) in the processing image 818B can be used to confirm the correct scale was applied and perspective was sufficiently removed. Further, while FIG. 8 depicts the use of a conventional sheet of paper for the scale object 828, this disclosure is not so limited. Further, other measurements of the scale object 828 can be used to determine scaling. For example, in some implementations, the scale attributes 852 can be the measured top and bottom widths of the scale object 828 and the left and right heights of the scale object 828. The top and bottom widths of the scale object 828 can be averaged to determine a scale in the X direction and the left and right heights of the scale object 828 can be averaged to determine a scale in the Y direction. Determining both an X direction scale and a Y direction scale for the processed image 818B can increase overall accuracy, especially when the pixels of the processed image 818B are not square, such as with video images.

The processed imaged 818B also schematically shows example physical attributes 854 of the subject 826 that can be ascertained during the image processing 842. In the illustrated embodiment, various joint locations and physical features (i.e., ear location, eye locations, naval location, etc.) are determined. Such determination can be performed by the disposable article recommendation computing system 800 or it can be performed locally, remotely by a third party computing system, or by any other suitable resource. In some implementations, machine learning-based models are utilized to identify joint locations or other types of physical features. An example resource for determining joint locations for a subject image is provided by OpenPose offered by Carnegie Mellon University, Pittsburgh, Pennsylvania. OpenPose is a real-time multi-person system to jointly detect human body, hand, facial, and foot keypoints on single images. Other techniques for detecting physical attributes 854 of the user can include edge detection and object detection algorithms. By way of example, alternatively or additionally to determining joint locations, algorithms may be used to identify a triangle created by the nipples and naval of the subject 826. Based on the dimensions of that triangle, as determined based on the scale of the image, models can be applied to determine appropriate sizing for the subject 826.

Once the physical attributes 854 have been identified, the disposable article recommendation computing system 800 can determine various dimensions of the subject 826 based on the scale. While the determined dimensions can vary based on the physical attributes 854, in some implementations, example dimensions include a torso measurement, distance between ears, shoulder width, and a hip width.

During product fit processing 844, various fit parameters can be determined by the disposable article recommendation computing system 800 based on the dimensions associated with the physical attributes 854. The particular fit parameters utilized by disposable article recommendation computing system 800 then can be selected to match fit parameters of various sizing models 808. For instance, the sizing models 808 can each be defined by acceptable ranges of certain fit parameters, such as, without limitation, a waist circumference at the naval, a rise measurement from naval to back, and a thigh circumference. Thus, the disposable article recommendation computing system 800 can estimate fit parameters based on the determined dimensions of the physical attributes 854. In some embodiments, statistical models are used to correlate the various dimensions of the physical attributes 854 to the various fit parameters or directly to a preferred diaper size, for example. Furthermore, in some embodiments, beyond the various dimensions of the physical attributes 854 ascertained through image analysis, other inputs to the statistical model can include gender and age, as well as other specific dimensions or information entered by a user, as described in more detail below.

Referring now to FIG. 9, example fit parameters 956 are shown that are based on physical attributes 954. In the illustrated embodiment, the fit parameters 956 include a waist circumference at the naval, a rise measurement from naval to back, and a thigh circumference. Similar to FIG. 8, the fit parameters 956 are based on the physical attributes 954 of a subject, which are shown as joint locations, eye locations, and so forth, as well as a scale object 928. FIGS. 10-11, however, show that other methodologies can be used to determine a scale of the image. Referring to FIG. 10, an example process for determining a scale and fit parameters is based on a body part dimension, as provided by a user of a disposable article recommendation computing system. For example, in the illustrated embodiment, a foot size 1054 is provided by the user to a disposable article recommendation computing system. The foot size 1054 can be provided in any suitable format, such as a shoe size or foot length. The disposable article recommendation computing system can utilize the known dimension of the subject's foot to determine a scale for the image when the foot of the subject is captured at an appropriate angle within the image. Based on scale and the physical attributes of the subject, various fit parameters 1056 can be determined. FIG. 11 depicts another configuration in which a head circumference is provided to a disposable article recommendation computing system by a user. Similar to FIG. 10, leveraging a known dimension of the subject, or a parameter such as head width 1154 as calculated from the known head circumference, the disposable article recommendation computing system can determine the scale of the image. In turn, the disposable article recommendation computing system can then determine the fit parameters 1156. In other embodiments, one or more of the fit parameters can additionally or alternately be provided by the user, such as a waist dimension or a height in order to scale the image. With regard to height, for example, the height of the subject in the image can be calculated from the sum of joint distances. Moreover, interocular distance or eye diameter can be useful to scale the image, as these dimensions have very little variance in the population, and only change very slowly with age. By way of example, an eyeball diameter for newborns is 16 mm+/−2 mm and the eyeball diameter for 3 yr olds is 19 mm+/−2 mm. So upon receipt of the subject's age, an age vs. eyeball diameter curve can be utilized by the disposable article recommendation computing system to identify the eyeball diameter within a few mm of the correct scale.

Other techniques or technologies also may be used for determining a scale of an image, such as photogrammetry. Two or more images can be taken of a subject from two or more known locations, with the size of objects within the photograph calculated by tracking of reference points. Alternately, multiple lenses on a single device can capture images which can be used for photogrammetry processes. Another approach is to utilize a single camera that moves through space with measures of where the camera is moving. Alternately, point clouds or structured light may be used. In this approach, a known pattern of stripes or an array of dots can be projected out onto a target area/subject. Then a camera can read the deformation of the projected light as it lands on different 3D objects. Using algorithms, the 3D shapes and dimensions of those objects may be calculated based on the measured deformation of the known light patterns. The structured light may be visible, IR, or other wavelengths as long as the camera configured for this purpose can detect the deformed light pattern. Alternately, depth sensors can be used to calculate distance to an object and calculate scale based on how many pixels a relatively flat object (such as a baby or part of a baby body) occupies in the image and using triangulation or trigonometry to calculate scale. Alternately, tilt sensors, position sensors, accelerometers, or other sensors from a smart phone or other device may be incorporated into the approach to aid with calculation of scale in an acquired image or 3D scan.

Figure 12:
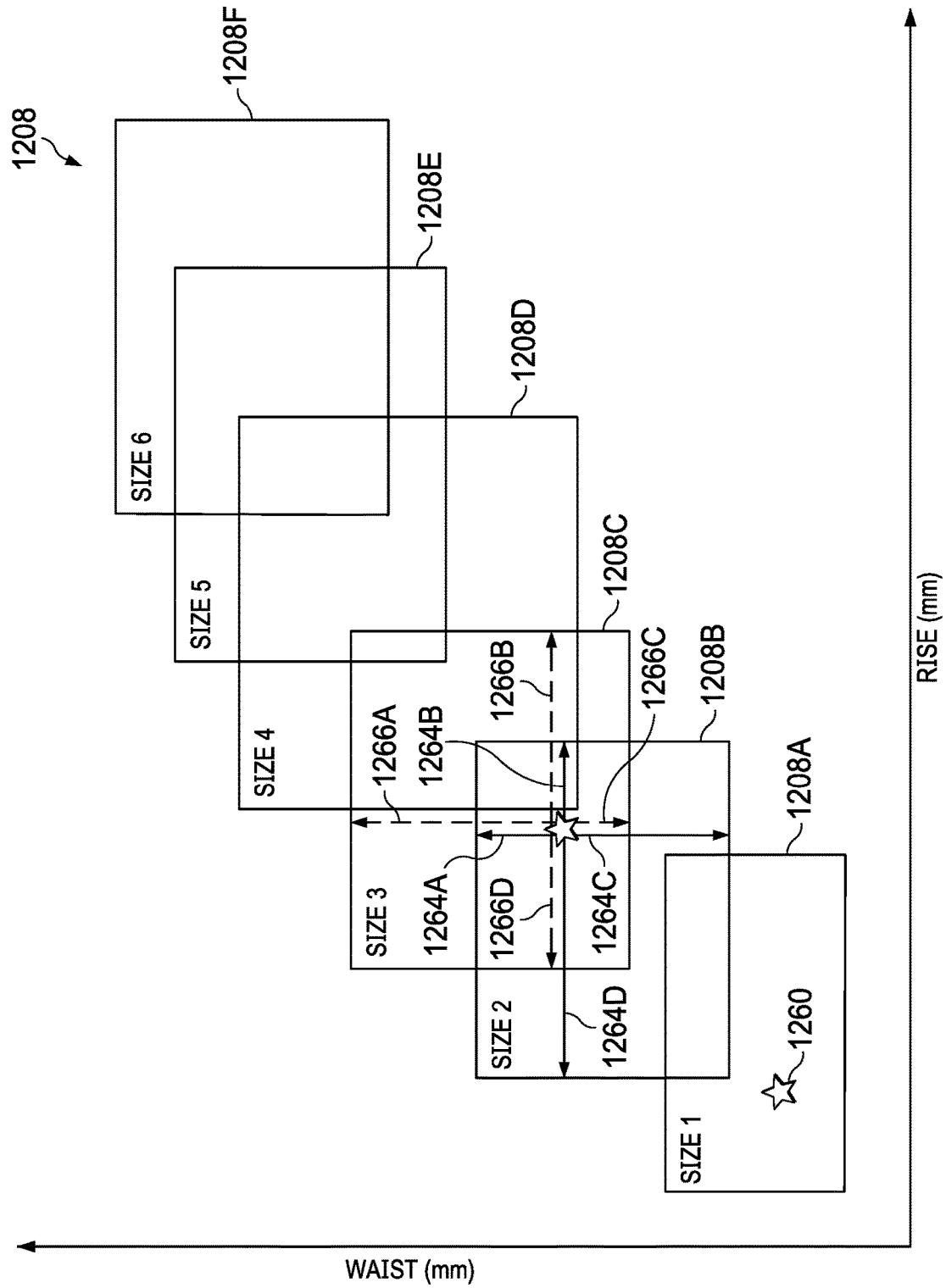
FIG. 12 depicts simplified sizing models for a lineup of disposable articles.

Referring now to FIG. 12, simplified sizing models 1208 for sizes 1 through 6 of an example product lineup of disposable articles are schematically depicted. While each of the sizing models 1208A-1208F are defined in terms of waist dimension and rise dimensions, this disclosure is not so limited. For example, the sizing models 1208A-1208F can include additional dimensions, such as thigh circumference, or be based on different dimensions. In any event, in accordance with the present disclosure, a disposable article recommendation computing system can apply the fit parameters of the subject, as determined through image analysis, to the sizing models 1208 to determine which size or sizes of the disposable article can be worn by the subject.

FIG. 12 graphically shows example fit parameters for two different subjects, shown as subject 1260 and subject 1262. Referring first to the fit parameters defined by the subject 1260, the disposable article recommendation computing system can determine that the subject 1260 falls within the sizing model 1208A for a size 1 disposable articles and provide such a recommendation to a user. The fit parameters defined by the subject 1262, however, cause the subject 1262 to fall within multiple sizing models, namely, the size 2 sizing model 1208B and the size 3 sizing model 1208C. Various approaches can be used by a disposable article recommendation computing system to determine which of these two sizes to recommend to a user. In accordance with the illustrated embodiment, the disposable article recommendation computing system determines the relative distance from the fit parameters defined by the subject 1262 to each of the boundaries of the implicated sizing models. In the illustrated embodiment, distances 1266*a-d* are the distances to the boundaries of the size 3 sizing model 1208C and distances 1264*a-d* are the distances to the boundaries of the size 2 sizing model 1208B. More particularly, distances 1266*a* and 1266*c* are the distances to the upper and lower bounds of the waist fit parameter for the size 3 sizing model 1208C. Distances 1266*b* and 1266*d* are the distances to the upper and lower bounds of the rise fit parameter for the size 3 sizing model 1208C. Distances 1264*a* and 1264*c* are the distances to the upper and lower bounds of the waist fit parameter for the size 2 sizing model 1208B. Distances 1264*b* and 1264*d* are the distances to the upper and lower bounds of the rise fit parameter for the size 2 sizing model 1208B.

Once the distances 1266*a-d* and 1264*a-d* are determined, the disposable article recommendation computing system can recommend the disposable article size based on the measured distances. In some embodiments, for example, the disposable article recommendation computing system can identify the smallest dimension of all the boundary dimensions 1266*a-d* and 1264*a-d* for each sizing models 1208B and 1208C. The disposable article recommendation computing system can then compare those two smallest dimensions, and recommend the sizing model that has the largest of those dimensions.

Figure 13:
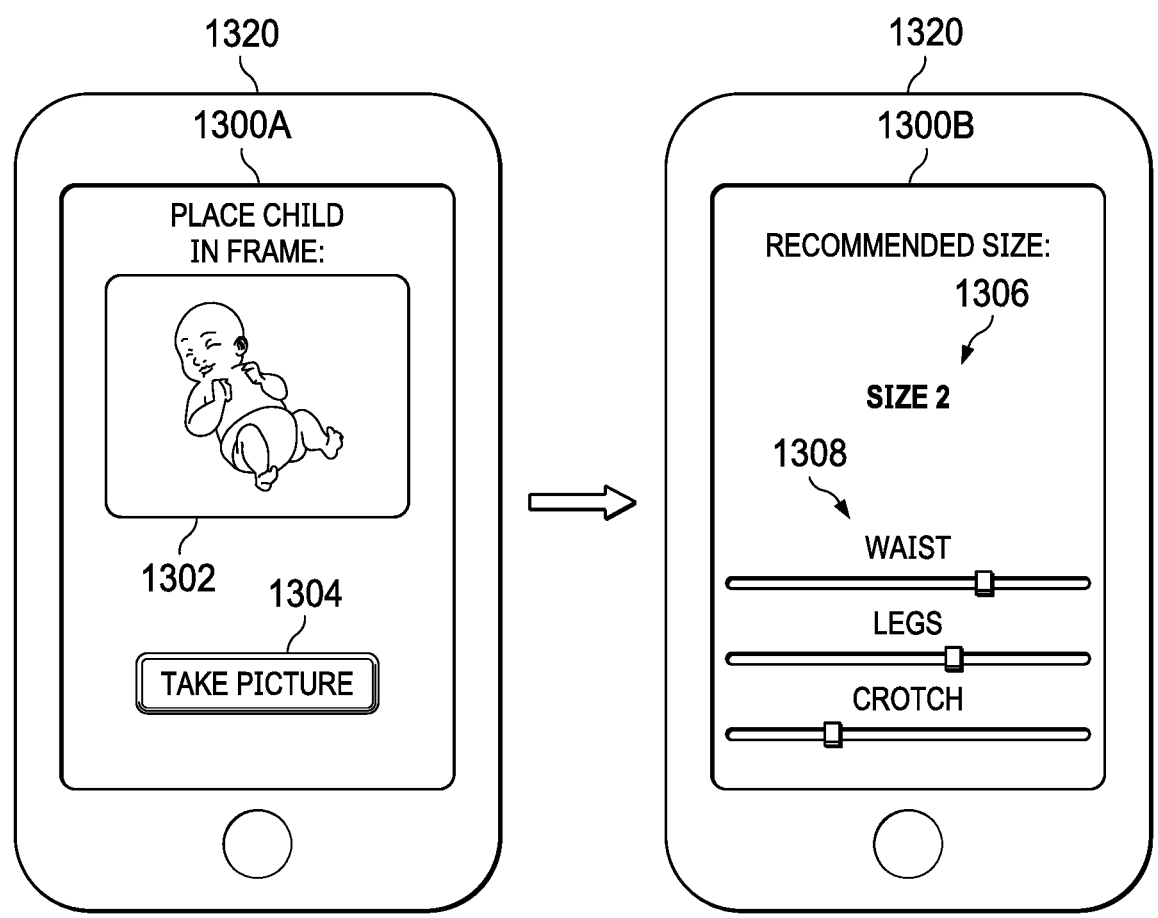
FIG. 13 depicts a series of simplified interfaces for image collection and displaying of a recommendation.

FIGS. 13-20 depict simplified example user interface displays on various computing devices in accordance with non-limiting embodiments. The user interface displays can be a component of, for example, the disposable article recommendation computing system 100 of FIG. 1 or any the remote computing devices 238, 438, 538, 638, 738 of FIG. 2 and FIGS. 4-6. Referring first to FIG. 13, a series of interfaces 1300A-1300B are shown that can be presented on a computing device 1320. The interface 1300A shows an example image preview pane 1302 during an image collection process. The image preview pane 1302 can be used to properly align a subject in the field of view. In some embodiments, the image preview pane 1302 can include graphical guides or other type of feedback to assist the user with alignment, such as augmented reality. As shown, an interactive element 1304 can be activated by a user to take a picture, or series of pictures, of the subject. The image collected by the computing device 1320 can be processed in accordance with the present disclosure and the user can be presented with the interface 1300B. The interface 1300B can present a recommendation 1306 in any suitable format. As is to be appreciated, the recommendation 1306 can comprise a variety of information associated with the recommendation, such as recommended product type, recommended product lineup, and so forth. In some embodiments, the interface 1300B can also include fit metrics 1308. The fit metrics 1308 can indicate how the recommended disposable article is expected to fit the subject. The fit metrics 1308 can be based on, for example, the relative location of the subject's fit parameters within the sizing model for the recommended size of disposable article.

Figure 14:
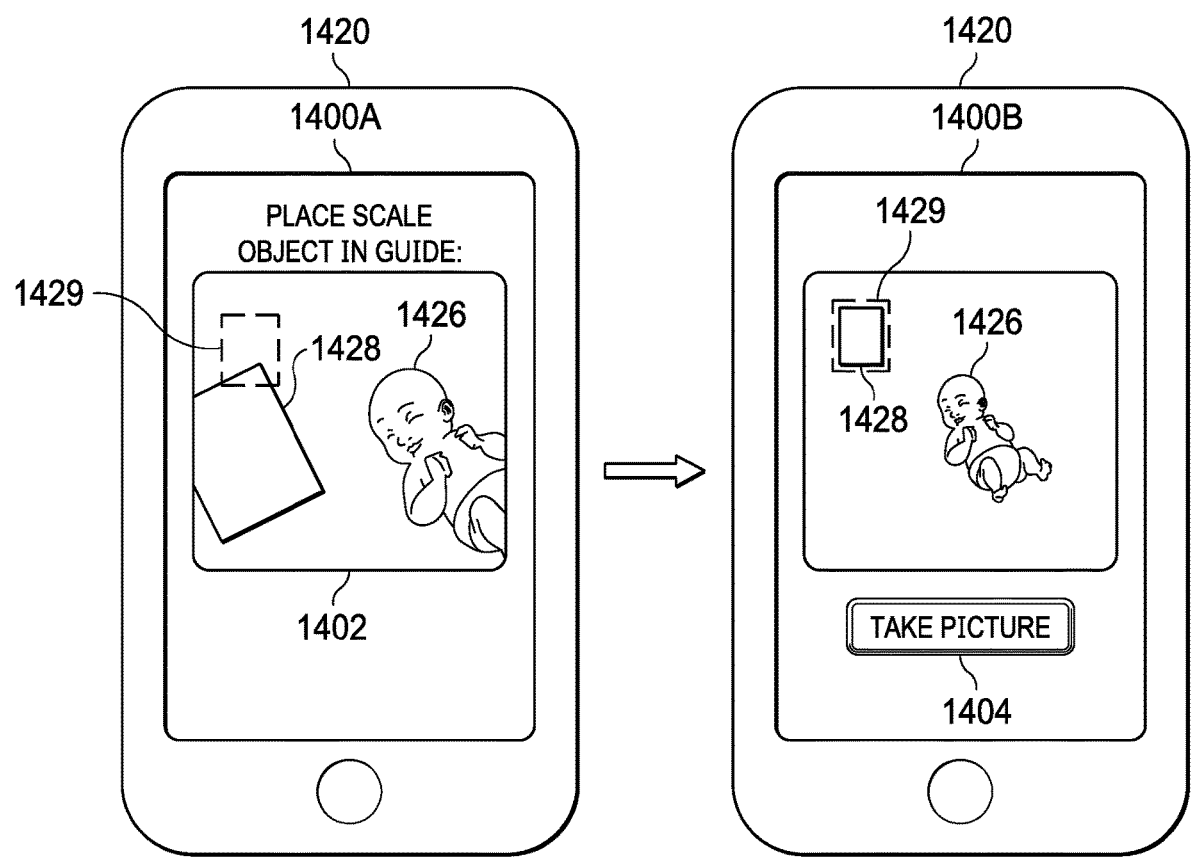
FIG. 14 depicts a series of simplified interfaces for image collection using a scale object graphical guide.

FIG. 14 depicts other example simplified interface 1400 that can be presented on a computing device 1420 by a disposable article recommendation computing system. The interface 1400A shows an example image preview pane 1402 during an image collection process. The image preview pane 1402 can be used to properly align a scale object 1428 in the field of view as well as guide the user to collect the image at a sufficient distance away from the subject 1426. In this example implementation the image preview pane 1402 includes a scale object graphical guide 1429 to assist the user with the image collection process. As shown with the interface 1400B, an interactive element 1404 can be presented to the user once proper alignment of the scale object 1428 and the scale object graphical guide 1429 is detected. The user is only permitted to collect an image after the scale object 1428 is properly positioned within the bounds of the scale object graphical guide 1429. The use of the scale object graphical guide 1429 can therefore give real-time feedback to the user to aid in the image collection process.

The use of the scale object graphical guide 1429 can ensure the subject 1426 is a sufficient distance from the computing device 1420. By forcing the user to collect an image from a particular distance the necessity of interpolating the scale of the subject 1426 in accordance with FIGS. 3A-3C, for example, may be reduced or eliminated. Additionally, the scale object graphical guide 1429 can also ensure that the relative angle between the computing device 1420 and the scale object 1428 is acceptable for processing, thereby avoiding the need for excessive correction for image keystoning due to perspective effects.

The scale object graphical guide 1429 can also direct the user to place the scale object 1428 in a particular orientation relative to the subject 1426. With reference to FIG. 14, the placement of the scale object graphical guide 1429 in the image preview pane 1402 ensures the scale object 1428 is placed to the upper left of the subject 1426. Guiding the user to place the scale object 1428 in a particular location can reduce overall variability in the collected images. Decreasing variability can improve overall accuracy, as the relative positioning of the scale object 1428 and the subject 1426 in the images can be selected to match the relative positioning of the images used the train the system and develop the models. Additionally or alternatively, graphical guides to assist with alignment and placement of subject can be used. Such graphical guides can direct the user to place the subject within a particular orientation (i.e., the head towards the top of the frame and the legs toward the bottom of the frame), which can help to reduce variability in collected images, for example.

Figure 15:
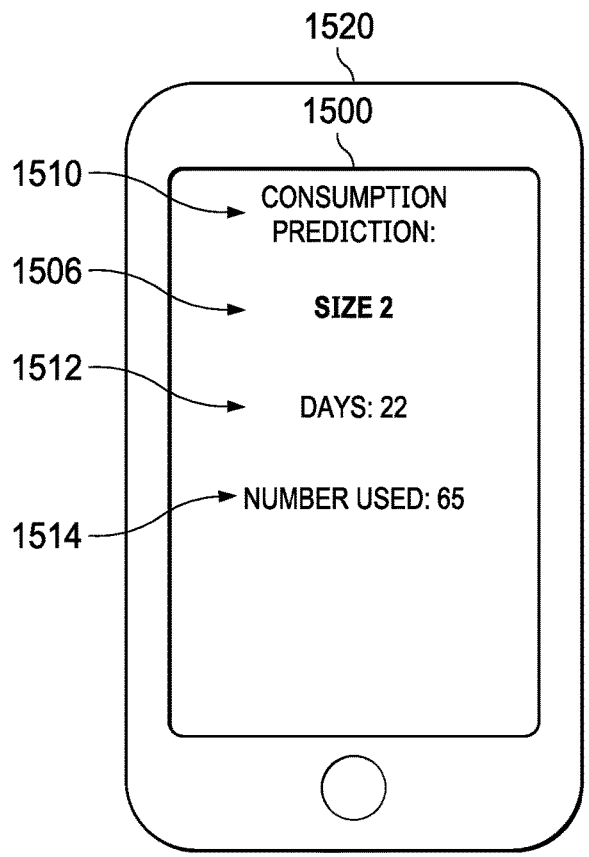
FIGS. 15-16 depict simplified interfaces displaying example consumption predictions.

FIG. 15 depicts another example simplified interface 1500 that can be presented on a computing device 1520 by a disposable article recommendation computing system. The interface 1500 can provide a disposable article consumption prediction 1510, as determined by the disposable article recommendation computing system. Disposable article consumption predictions 1510 can include a variety of information, such as a predicted rate of consumption (i.e., number of absorbent articles used over a period of time) and/or an amount of time until the wearer will need to move to a different size and/or product line. In the illustrated embodiment, for example, the disposable article consumption prediction 1510 includes a recommended size 1506, a time period prediction 1512, and a quantity prediction 1514 based on the predicted rate of consumption. Thus, the disposable article consumption prediction 1510 informs the user that the subject is expected to be wearing a size 2 disposable article for the next 22 days and will consume 65 articles in that time period. The model for determining such disposable article consumption prediction 1510 can be based on any number of inputs, include the subject's physical attributes, age, gender, growth history, projected Centers for Disease Control and Prevention (CDC) growth charts, and so forth. Some of the inputs can be determined based on image analysis while other may be based on user supplied information, such as information provided at the time of image submission or information that was previously submitted when creating a user profile, for example. In some embodiments, a series of images of the subject can be collected over time (i.e., greater than 3 days), with a growth pattern for the subject determined based on the subject's growth image to image. With regard to determining predicting consumption rates, various techniques can be used. For example, users can input information about when they buy absorbent articles, and how many they bought. This information can be collected using any suitable technique, such as the user manually providing the information through an interface or scanning a UPC code on a package of absorbent articles. Providing this information can be incentivized by tying the scanning of the UPC code to a rewards program, for example. In some embodiments, the user provides information regarding how many disposable articles they change per day. In some embodiments, statistical models are utilized that pertain to how many absorbent articles are used by wearers in a day, based on age. Further, while some of the consumption predictions are schematically shown as being a number of absorbent articles consumed, it can also be expressed in terms of number of packages of absorbent articles. Consumption predictions expressed in terms of package consumption can take package configuration into consideration, as the number of absorbent articles that are contained within a package may vary based on absorbent articles size, product lineup, and so forth.

Recommendations provided by the disposable article recommendation computing system may also include a value calculation for the user that incorporates various elements of recommendations, such as how many disposable articles will be consumed, the number of trips to stores, among other consumption metrics to provide the best overall value to a user. With regard to automated shipments of products, the recommendation may include a timetable of shipments of various products in the product line up. The disposable article recommendation computing system can be configured to receive feedback from a user to provide information on how the recommendation was received. This feedback may be used to improve or otherwise refine that particular recommendation and/or to improve the quality of the overall models over time from collecting feedback across multiple users. Moreover, based on a disposable article consumption prediction, a disposable article recommendation computing system can dispatch notifications to a user when it is time to purchase additional disposable articles. Such notifications can be in any suitable format and dispatched through any suitable communication medium. In some embodiments, the notifications are text messages, email messages, in-app messages, calendar appointments, reminders, smart speaker notification, pop-up notifications, geofenced notifications (e.g. when physically near a store), or combinations thereof. Additionally, a subscription purchase program can be provided to the user, such that disposable articles are routinely sent to the user and the recommended size of the disposable article is automatically increased over time. In some configuration a bulk shipment is provided that contains an amount of disposable articles in all of the various sizes that are predicted to be used by a wearer over time.

Figure 16:
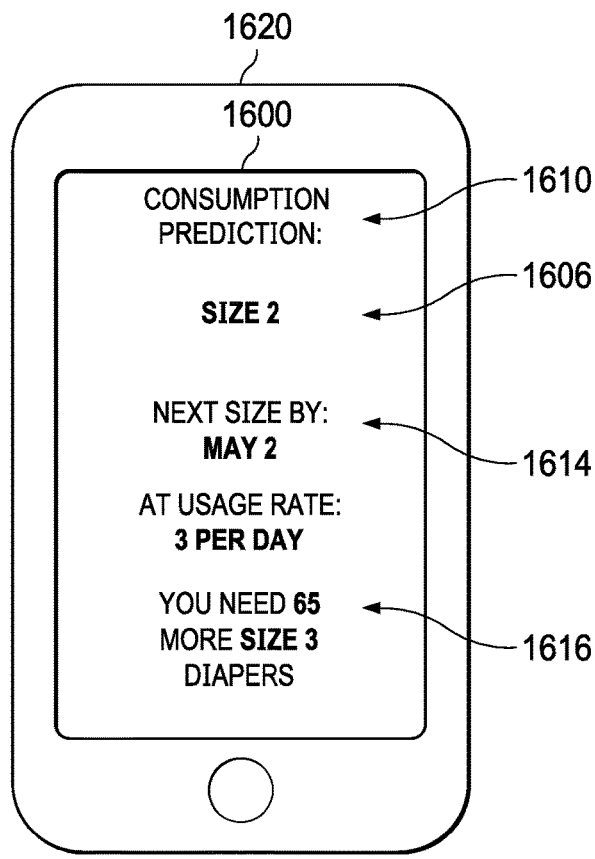

FIG. 16 depicts another example disposable article consumption prediction 1510 that can be displayed on an interface 1500 of a computing device 1520. The disposable article consumption prediction 1510 includes a recommended size 1506, a time period prediction 1514, and a quantity prediction 1516. In this embodiment, the time period prediction 1514 is expressed in terms of a date and the quantity prediction 1516 includes a usage rate. The usage rate may be tunable as an input such that the associated recommendations change with the user-provided input on rate, for example.

Figure 19:
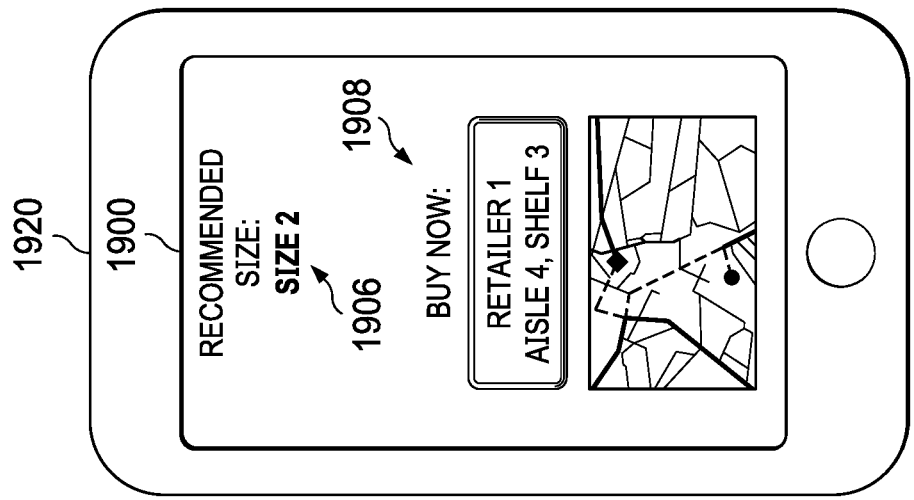
FIG. 17-19 depict simplified interfaces displaying example purchase pathways.
Figure 18:
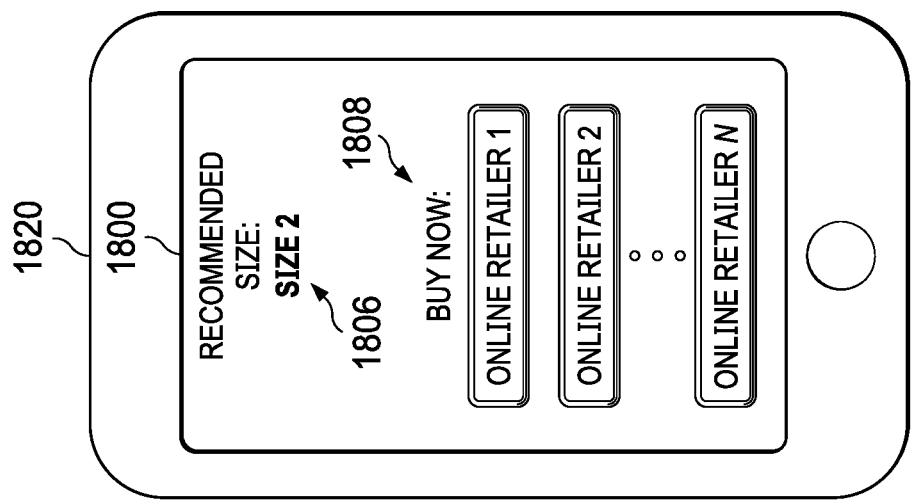
Figure 17:
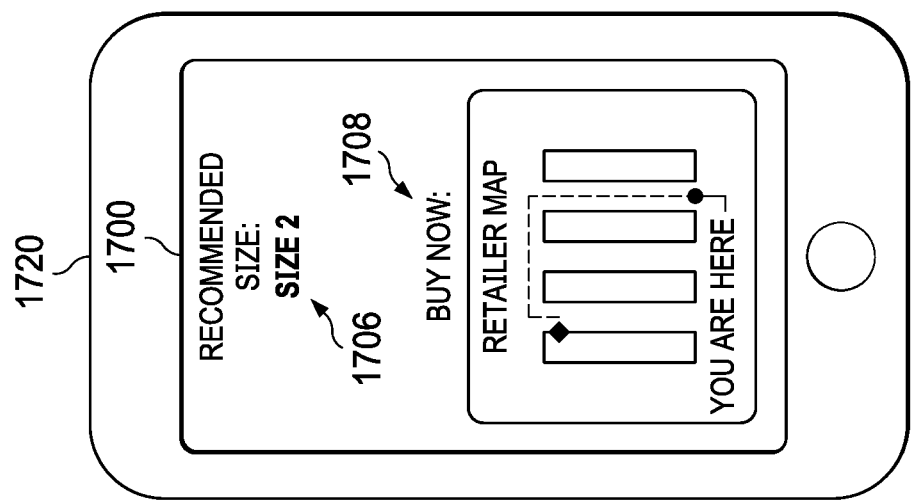

FIGS. 17-19 depict example indications of purchase pathways that can be provided to a user via an interface. The purchase pathway can be expressed in any suitable format. Referring first to FIG. 17, an example interface 1500 of a computing device 1720 shows a first example of a recommended size 1706 and a purchase pathway 1708. In this embodiment, the purchase pathway 1708 is a retailer map that provides real-time location information based on the GPS data provided by the computing device 1720. As such, the purchase pathway 1708 can guide the user to the aisle in the retailer to purchase the recommended size 1706 of disposable articles, and in some embodiments, provide additional information to the use such as quantity available, pricing data, and so forth. FIG. 18 depicts an example interface 1800 of a computing device 1820 that shows another example purchase pathway 1808 along with a recommended size 1806. The purchase pathway 1808 can include one or more web-based links to purchase the recommended size 1806 of disposable articles via an online retailer or online marketplace forum. FIG. 19 depicts an example interface 1900 of a computing device 1920 that shows another example purchase pathway 1908 along with a recommended size 1906. The purchase pathway 1908 in this embodiment can include a map that includes driving directions to direct the user to a retailer to purchase the disposable articles. As shown, additional purchase related information can be provided, such as aisle location, quantity available, pricing data, and so forth.

Referring now to FIG. 20, example simplified interfaces 2000A-C of a computing device 2020 are depicted. Interface 2000A schematically depicts the collection of a variety of inputs from a user that can be utilized by a disposable article recommendation computing system. Providing developmental milestones 2002 can assist the disposable article recommendation computing system with recommending the proper product line, for example. Example developmental milestones 2002 can include, without limitation, crawling, pulling up on furniture, walking, starting potty training, sleeping through the night, and so forth. Additionally or alternatively, user supplied inputs 2004 can be provided to the disposable article recommendation computing system to aid in generating the recommendation. Example user supplied inputs 2004 can include, for example, weight, length, head size, birthday, a gestational age of the subject at birth, and so forth. Additional inputs can include geographical location, as certain regions have different expectations when it comes to the fit of disposable articles. The geographical location can be ascertained based on the physical location of the user's computer device or it can be provided by the user as part of an enrollment process, for example. One or more inputs can be visualized and tracked alone or with population growth curves, such as the conventional CDC growth curves for children. The interface 2000B schematically depicts the collection of an image of subject. Similar to FIG. 13, the interface 2000B can have an example image preview pane 2006. The image preview pane 2006 can be used to properly align a subject in the field of view. An interactive element 2008 can be activated by a user to take a picture, or series of pictures, of the subject. The image collected by the computing device 2020 can be processed in accordance with the present disclosure and the user can be presented with the interface 2000C. The interface 2000C can present a recommendation 2010 in any suitable format. The recommendation 2010 can be based on both image analysis, as described herein, and the additional information provided by the user via the interface 2000A. As to be appreciated, the recommendation 2010 can comprise a recommended product type, recommended product lineup, and so forth. The example interface 2000C also includes fit metrics 2012 to indicate the how the recommended disposable article is expected to fit the subject.

Figure 21:
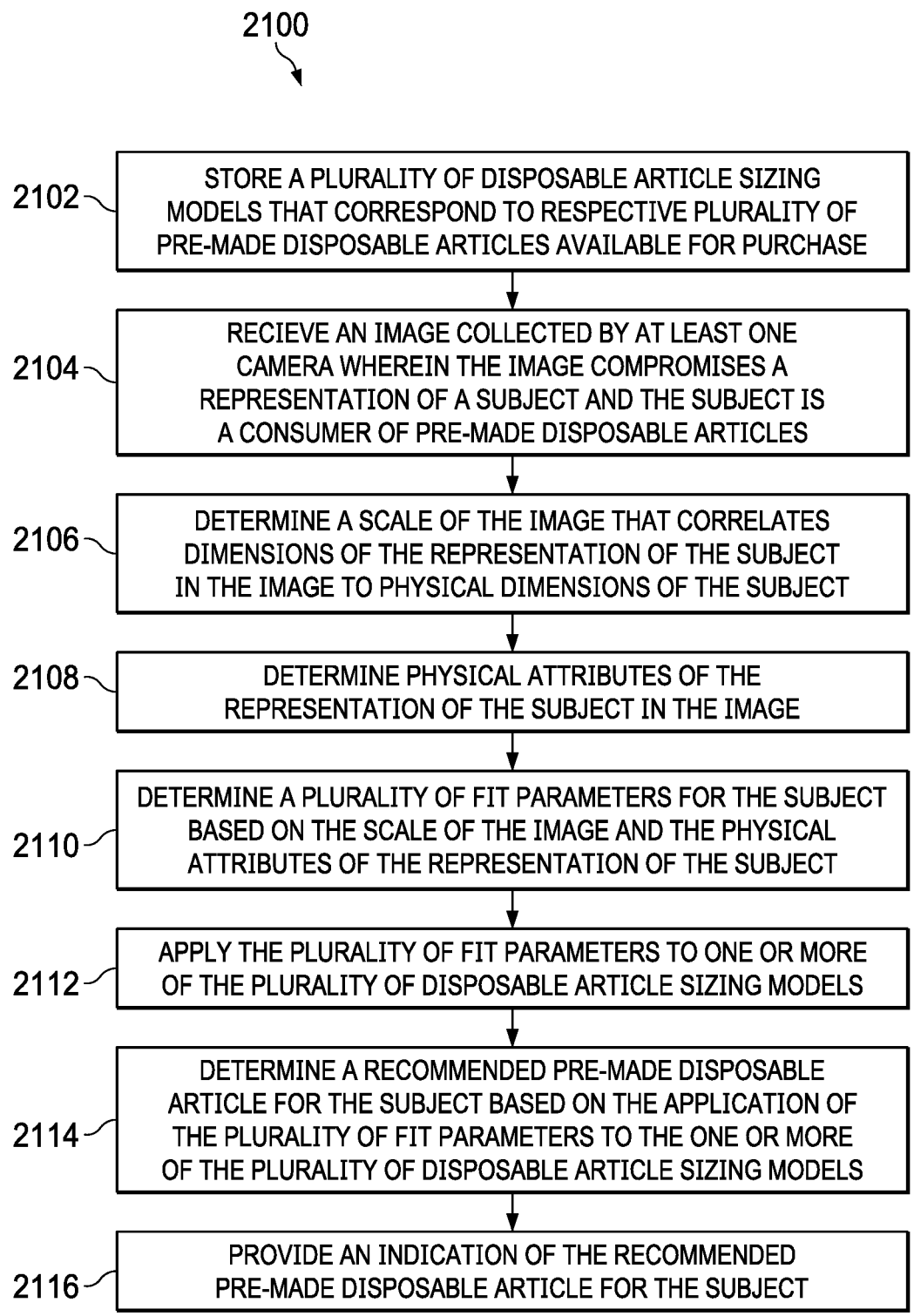
FIG. 21 is a flow chart for an example method of recommending a pre-made disposable article for a subject.

FIG. 21 depicts an example flow chart 2100 for a method of recommending a pre-made disposable article for a subject. At 2102, the method comprising storing a plurality of disposable article sizing models that correspond to respective plurality of pre-made disposable articles available for purchase. The sizing models can be stored by a disposable article recommendation computing system, as shown in FIGS. 1-6. In this regard, the sizing models can either be stored in a centralized repository or can be stored locally at end user computer devices. At 2104, an image collected by at least one camera is received. The image can comprise a representation of a subject. The subject is a consumer of pre-made disposable articles, such as an infant, a baby, or a toddler. The received image can be a still image, a collection of still images, or a video, for example.

At 2106, a scale of the image correlating dimensions of the representation of the subject in the image to physical dimensions of the subject is determined. The scale can be determined through any suitable technique, such as utilizing a scale object in the image or inferring the scale based on the known body part dimension of the subject in the image, such as a height of the subject, an intra-pupil distance of the subject, or a head circumference, for example. At 2108, physical attributes of the representation of the subject in the image are determined. As described above, physical attributes can include a plurality of joint locations of the subject, a distance between detected aspects of the representation of the subject in the image, as well as an area of the subject, or other quantifiable measurement of an aspect of the representation of the subject in the image.

At 2110, a plurality of fit parameters for the subject are determined based on the scale of the image and the physical attributes of the representation of the subject. The fit parameters can include, for example, an estimated waist circumference of the subject, an estimated thigh circumference of the subject, and an estimated rise measurement of the subject. At 2112, the plurality of fit parameters are applied to one or more of the plurality of disposable article sizing models. For instance, it can be determined which sizing model(s) captures each of the estimated waist circumference of the subject, the estimated thigh circumference of the subject, and the estimated rise measurement of the subject.

At 2114, based on the application of the plurality of fit parameters to the one or more of the plurality of disposable article sizing models, a recommended pre-made disposable article for the subject is determined. The recommended pre-made disposable article is selected from the plurality of pre-made disposable articles available for purchase. At 2116, an indication of the recommended pre-made disposable article for the subject is provided to a user.

Combinations

A. A computer-based method, comprising:
   storing, by a disposable article recommendation computing system in data store, a plurality of disposable article sizing models that correspond to respective plurality of pre-made disposable articles available for purchase;
   receiving, by the disposable article recommendation computing system, an image collected by at least one camera, wherein the image comprises a representation of a subject and the subject is a consumer of pre-made disposable articles;
   determining, by the disposable article recommendation computing system, a scale of the image that correlates dimensions of the representation of the subject in the image to physical dimensions of the subject;
   determining, by the disposable article recommendation computing system, physical attributes of the representation of the subject in the image;
   based on the scale of the image and the physical attributes of the representation of the subject, determining, by the disposable article recommendation computing system, a plurality of fit parameters for the subject;
   applying, by the disposable article recommendation computing system, the plurality of fit parameters to one or more of the plurality of disposable article sizing models;
   based on the application of the plurality of fit parameters to the one or more of the plurality of disposable article sizing models, determining, by the disposable article recommendation computing system, a recommended pre-made disposable article for the subject, wherein the recommended pre-made disposable article is selected from the plurality of pre-made disposable articles available for purchase; and
   providing, by the disposable article recommendation computing system, an indication of the recommended pre-made disposable article for the subject.

B. The computer-based method according to Paragraph A, wherein the recommended pre-made disposable article for the subject comprises any of a recommended standard size of a pre-made disposable article, a recommended product line of a pre-made disposable article, and a recommended style of pre-made disposable article.

C. The computer-based method according to any of Paragraphs A through B, wherein the image comprises a scale object positioned proximate to the representation of the subject.

D. The computer-based method according to Paragraph C, wherein the physical dimensions of the scale object in the image are known to the disposable article recommendation computing system.

E. The computer-based method according to any of Paragraphs A through D, wherein determining the scale of the image comprises determining an X direction scale and a Y direction scale.

F. The computer-based method according to any of Paragraphs A through E, further comprising:
   prior to determining the plurality of fit parameters, processing, by the disposable article recommendation computing system, the image to account for a perspective angle between the subject and the at least one camera.

G. The computer-based method according to any of Paragraphs A through F, wherein the physical attributes comprise a plurality of joint locations of the subject.

H. The computer-based method according to Paragraph G, wherein the plurality of joint locations of the subject are determined based at least partially on a machine learning model.

I. The computer-based method according to any of Paragraphs A through H, wherein the physical attributes comprise a distance between detected aspects of the representation of the subject in the image.

J. The computer-based method according to any of Paragraphs A through I, wherein the physical attributes comprise any of a length, a width, an area, and a volume of an aspect of the representation of the subject in the image.

K. The computer-based method according to any of Paragraphs A through J, wherein the plurality of fit parameters are based on correlations to one or more of the physical attributes of the subject.

L. The computer-based method according to any of Paragraphs A through K, wherein the physical attributes comprise any of a head width, an eye separation distance, a torso length, a hip width, and a shoulder width.

M. The computer-based method according to any of Paragraphs A through L, wherein the fit parameters comprise any of an estimated waist circumference of the subject, an estimated thigh circumference of the subject, and an estimated rise measurement of the subject.

N. The computer-based method according to Paragraph M, wherein each of the plurality of disposable article sizing models comprises a waist circumference range, a thigh circumference range, and a rise measurement range.

O. The computer-based method according to Paragraph N, wherein applying the plurality of fit parameters to one or more of the plurality of disposable article sizing models comprises determining, for each respective disposable article sizing model, whether the estimated waist circumference is within the waist circumference range, the estimated thigh circumference is within the thigh circumference range, and the estimated rise measurement is within the rise measurement range.

P. The computer-based method according to Paragraph O, wherein the recommended pre-made disposable article for the subject is one of a plurality of different pre-made disposable articles that are determined to be sized for the subject.

Q. The computer-based method according to any of Paragraphs A through P, further comprising:
receiving, by the disposable article recommendation computing system, one or more user supplied values.

R. The computer-based method according to Paragraph Q, wherein the user supplied values comprise any of an age of the subject, a weight of the subject, a race of the subject, a gender of the subject, a height of the subject, a gestational age of the subject at birth, and a head circumference of the subject.

S. The computer-based method according to any of Paragraphs A through R, further comprising:
determining, by the disposable article recommendation computing system, a disposable article consumption prediction; and
providing, by the disposable article recommendation computing system, the disposable article consumption prediction.

T. The computer-based method according to Paragraph S, wherein the disposable article consumption prediction is based on one or more of the user supplied values.

U. The computer-based method according to Paragraph T, wherein the disposable article consumption prediction is based on one or more of the user supplied values and one or more of the determined physical attributes.

V. The computer-based method according to any of Paragraphs R through U, wherein the disposable article consumption prediction comprises an estimated number of the recommended pre-made disposable articles to be used by the subject.

W. The computer-based method according to any of Paragraphs R through V, wherein the disposable article consumption prediction is associated with any of a product, a product size, and a product lineup.

X. The computer-based method according to any of Paragraphs R through W, wherein the disposable article consumption prediction comprises an estimated amount of time the recommended pre-made disposable article will fit the subject.

Y. The computer-based method according to any of Paragraphs R through X, further comprising:
sending, by the disposable article recommendation computing system, a purchase reminder notification to a remote computing device based on the disposable article consumption prediction.

Z. The computer-based method according to any of Paragraphs R through Y, further comprising:
enrolling, by the disposable article recommendation computing system, a user into a subscription purchase program for pre-made disposable articles.

AA. The computer-based method according to any of Paragraphs R through Z, further comprising:
automatically increasing a recommended size of the recommended pre-made disposable articles after a period of time.

AB. The computer-based method according to any of Paragraphs A through AA, wherein the image is one or more still images of the subject collected by a mobile computing device.

AC. The computer-based method according to Paragraph AB, wherein the one or more still images of the subject are collected by a rear-facing camera of the mobile computing device.

AD. The computer-based method according to any of Paragraphs A through AC, further comprising:
receiving, by the disposable article recommendation computing system, a plurality of images of a subject collected over a period of time, wherein the period of time is greater than three days; and
based on a growth pattern of the subject determined from the plurality of images, predicting, by the disposable article recommendation computing system, a disposable article consumption prediction.

AE. The computer-based method according to Paragraph AD, further comprising:
based on the growth pattern of the subject determined from the plurality of images, predicting, by the disposable article recommendation computing system, a recommended pre-made disposable article size progression over time prediction.

AF. The computer-based method according to any of Paragraphs A through AE, further comprising:
providing, by the disposable article recommendation computing system, at least one image collection guidance tool.

AG. The computer-based method according to Paragraph AF, wherein the at least one image collection guidance tool comprises a graphical overlay for presentment to a user during image collection.

AH. The computer-based method according to Paragraph AF, wherein the at least one image collection guidance tool comprises a scale object graphical guide.

AI. The computer-based method according to any of Paragraphs A through AH, wherein processing the image to determine a scale of the image comprises utilizing a known body part size of the subject.

AJ. The computer-based method according to Paragraph AI, wherein the known body part size of the subject is any of a height of the subject, an intra-pupil distance of the subject, and a head circumference of the subject.

AK. The computer-based method according to any of Paragraphs A through AJ, wherein processing the image to determine a scale of the image comprises utilizing a plurality images of the subject in a photogrammetric process.

AL. The computer-based method according to any of Paragraphs A through AK, wherein processing the image to determine a scale of the image comprises analyzing a deformation of structured light projected onto the subject.

AM. The computer-based method according to any of Paragraphs A through AL, further comprising:
determining, by the disposable article recommendation computing system, a geographic location of the subject, wherein the recommended pre-made disposable article for the subject is based on the geographic location.

AN. The computer-based method according to any of Paragraphs A through AM, wherein the image is a full-body overhead view of the subject, and wherein the subject is any of an infant, a baby, and a toddler.

AO. The computer-based method according to Paragraph AN, wherein the subject is laying on their back in the image.

AP. The computer-based method according to Paragraph AO, further comprising:
verifying, by an error checking module the disposable article recommendation computing system, one or more verification parameters of the image.

AQ. The computer-based method according to Paragraph AP, wherein verifying the verification parameters comprise any of verifying a presence of baby, a pose of baby, a presence of scale object, an orientation and perspective of a camera relative to a scale object, and an orientation and perspective of a camera relative to subject.

AR. The computer-based method according to Paragraph AO, wherein verifying the verification parameters comprise any of verifying physical attributes of the scale object.

AS. The computer-based method according to Paragraph AR, further comprising downsampling the image prior to verifying physical attributes of the scale object.

AT. The computer-based method according to any of Paragraphs A through AS, further comprising:
providing, by the disposable article recommendation computing system, an indication of a purchase pathway for the recommended pre-made disposable article for the subject.

AU. The computer-based method according to any of Paragraphs A through AT, wherein pre-made disposable article is any of a disposable diaper and disposable training pants.

AV. The computer-based method according to any of Paragraphs A through AU, wherein the image collected by the at least one camera is a single image.

AW. A computer-based system, comprising:
a data store, wherein a plurality of disposable article sizing models that correspond to respective sizes of a pre-made disposable articles available for purchase are stored by the data store; and
a disposable article recommendation computing system comprising computer-readable medium having computer-executable instructions stored thereon, the computer-executable instructions configured to instruct one or more computer processors to perform the following operations:
receive an image of a subject collected by a remote mobile computing device;
determine a scale of the image;
process the image to determine physical attributes of the subject;
based on the scale of the image and the physical attributes of the subject, determine a plurality of fit parameters for the subject;
compare the plurality of fit parameters to one or more of the plurality of disposable article sizing models;
based on the comparison of the plurality of fit parameters to the one or more of the plurality of disposable article sizing models, determine a recommended pre-made disposable article for the subject; and
send an indication of the recommended pre-made disposable article to the remote mobile computing device.

AX. The computer-based system according to Paragraph AW, wherein the recommended pre-made disposable article for the subject comprises any of a recommended standard size of a pre-made disposable article, a recommended product line of a pre-made disposable article, and a recommended style of pre-made disposable article.

AY. The computer-based system according to any of Paragraphs AW through AX, wherein the image comprises a scale object positioned proximate to the representation of the subject.

AZ. The computer-based system according to Paragraph AY, wherein the physical dimensions of the scale object in the image are known to the disposable article recommendation computing system.

BA. The computer-based system according to Paragraph AZ, wherein the physical dimensions of the scale object in the image known to the disposable article recommendation computing system comprise any of a corner-to-corner dimension, a height dimension, a width dimension, and a radius dimension.

BB. The computer-based system according to any of Paragraphs AW through BA, wherein the computer-executable instructions are further configured to instruct one or more computer processors to perform the following operations:
prior to determining the plurality of fit parameters, process the image to account for a perspective angle between the subject and the at least one camera.

BC. The computer-based system according to any of Paragraphs AW through BB wherein the physical attributes comprise a plurality of joint locations of the subject.

BD. The computer-based system according to Paragraph BC, wherein the plurality of joint locations of the subject are determined based at least partially on a machine learning model.

BE. The computer-based system according to any of Paragraphs AW through BD, wherein the physical attributes comprise a distance between detected aspects of the representation of the subject in the image.

BF. The computer-based system according to any of Paragraphs AW through BE, wherein the physical attributes comprise any of a circumference, an area, and a volume of an aspect of the representation of the subject in the image.

BG. The computer-based system according to any of Paragraphs AW through BF, wherein the plurality of fit parameters are based on correlations to one or more of the physical attributes of the subject.

BH. The computer-based system according to any of Paragraphs AW through BG, wherein the physical attributes comprise any of a head width, an eye separation distance, a torso length, a hip width, and a shoulder width.

BI. The computer-based system according to any of Paragraphs AW through BH, wherein the fit parameters comprise any of an estimated waist circumference of the subject, an estimated thigh circumference of the subject, and an estimated rise measurement of the subject.

BJ. The computer-based system according to Paragraph BI, wherein each of the plurality of disposable article sizing models comprises a waist circumference range, a thigh circumference range, and a rise measurement range.

BK. The computer-based system according to Paragraph BJ, wherein the comparison of the plurality of fit parameters to one or more of the plurality of disposable article sizing models comprises determining, for each respective disposable article sizing model, whether the estimated waist circumference is within the waist circumference range, the estimated thigh circumference is within the thigh circumference range, and the estimated rise measurement is within the rise measurement range.

BL. The computer-based system according to Paragraph BK, wherein the recommended pre-made disposable article for the subject is one of a plurality of different pre-made disposable articles that are determined to be sized for the subject.

BM. The computer-based system according to any of Paragraphs AW through BL, wherein the computer-executable instructions are further configured to instruct one or more computer processors to perform the following operations:
receive one or more user supplied values as entered into the remote computing device.

BN. The computer-based system according to Paragraph BM, wherein the user supplied values comprise any of an age of the subject, a weight of the subject, a race of the subject, a gender of the subject, a height of the subject, a gestational age of the subject at birth, and a head circumference of the subject.

BO. The computer-based system according to any of Paragraphs BM through BN, wherein the computer-executable instructions are further configured to instruct one or more computer processors to perform the following operations:
determine a disposable article consumption prediction; and
provide the disposable article consumption prediction to the remote mobile computing device.

BP. The computer-based system according to Paragraph BO, wherein the disposable article consumption prediction is based on one or more of the user supplied values.

BQ. The computer-based system according to Paragraph BP, wherein the disposable article consumption prediction is based on one or more of the user supplied values and one or more of the determined physical attributes.

BR. The computer-based system according to any of Paragraphs BO through BQ, wherein the disposable article consumption prediction comprises an estimated number of the recommended pre-made disposable articles to be used by the subject.

BS. The computer-based system according to any of Paragraphs BO through BR, wherein the disposable article consumption prediction is associated with any of a product, a product size, and a product lineup.

BT. The computer-based system according to any of Paragraphs BO through BS, wherein the disposable article consumption prediction comprises an estimated amount of time the recommended pre-made disposable article will fit the subject.

BU. The computer-based system according to any of Paragraphs BO through BT, wherein the computer-executable instructions are further configured to instruct one or more computer processors to perform the following operation:
send a purchase reminder notification to the remote computing device based on the disposable article consumption prediction.

BV. The computer-based system according to any of Paragraphs BO through BU, wherein the computer-executable instructions are further configured to instruct one or more computer processors to perform the following operation:
enroll a user into a subscription purchase program for pre-made disposable articles.

BW. The computer-based system according to any of Paragraphs BO through BV, wherein the computer-executable instructions are further configured to instruct one or more computer processors to perform the following operation:
automatically increasing a recommended size of the recommended pre-made disposable articles after a period of time.

BX. The computer-based system according to any of Paragraphs AW through BW, wherein the image is one or more still images of the subject collected by the remote mobile computing device.

BY. The computer-based system according to Paragraph BX, wherein the one or more still images of the subject are collected by a rear-facing camera of the remote mobile computing device.

BZ. The computer-based system according to any of Paragraphs AW through BY, wherein the computer-executable instructions are further configured to instruct one or more computer processors to perform the following operations:
receive a plurality of images of a subject collected over a period of time, wherein the period of time is greater than three days; and
based on a growth pattern of the subject determined from the plurality of images, predict a disposable article consumption prediction.

CA. The computer-based system according to Paragraph BZ, wherein the computer-executable instructions are further configured to instruct one or more computer processors to perform the following operation:
based on the growth pattern of the subject determined from the plurality of images, predict a recommended pre-made disposable article size progression over time prediction.

CB. The computer-based system according to any of Paragraphs AW through CA, wherein the computer-executable instructions are further configured to instruct one or more computer processors to perform the following operation:
provide at least one image collection guidance tool.

CC. The computer-based system according to Paragraph CB, wherein the at least one image collection guidance tool comprises a graphical overlay for presentment to a user during image collection.

CD. The computer-based system according to any of Paragraphs AW through CC, wherein processing the image to determine a scale of the image comprises utilizing a known body part size of the subject.

CE. The computer-based system according to Paragraph CD, wherein the known body part size of the subject is any a height of the subject and a head circumference of the subject.

CF. The computer-based system according to any of Paragraphs AW through CE, wherein processing the image to determine a scale of the image comprises utilizing a plurality images of the subject in a photogrammetric process.

CG. The computer-based system of any of Paragraphs AW through CF, wherein processing the image to determine a scale of the image comprises accounting for the vertical separation between a plane of the scale object and a plane within which physical attributes of the subject lie.

CH. The computer-based system according to any of Paragraphs AW through CG, wherein processing the image to determine a scale of the image comprises analyzing a deformation of structured light projected onto the subject.

CI. The computer-based system according to any of Paragraphs AW through CH, wherein the computer-executable instructions are further configured to instruct one or more computer processors to perform the following operation:
determine a geographic location of the subject, wherein the recommended pre-made disposable article for the subject is based on the geographic location.

CJ. The computer-based system according to any of Paragraphs AW through CI, wherein the image is a full-body overhead view of the subject, and wherein the subject is any of an infant, a baby, and a toddler.

CK. The computer-based system according to Paragraph CJ, wherein the subject is laying on their back in the image.

CL. The computer-based system according to Paragraph CK, wherein the computer-executable instructions are further configured to instruct one or more computer processors to perform the following operation:
verifying one or more verification parameters of the image.

CM. The computer-based system according to Paragraph CL, wherein verifying the verification parameters comprise any of verifying a presence of baby, a pose of baby, a presence of scale object, an orientation and perspective of a camera relative to a scale object, and an orientation and perspective of a camera relative to subject.

CN. The computer-based system according to any of Paragraphs AW through CM, wherein the computer-executable instructions are further configured to instruct one or more computer processors to perform the following operation:
provide an indication of a purchase pathway for the recommended pre-made disposable article for the subject.

CO. The computer-based system according to any of Paragraphs AW through CN, wherein pre-made disposable article is any of a disposable diaper and disposable training pants.

CP. The computer-based system according to any of Paragraphs AW through CO, wherein the image received from the remote mobile computing device is a single image.

CQ. A computer-based method, comprising:
storing a plurality of disposable article sizing models that correspond to respective plurality of pre-made disposable articles available for purchase;
receiving an image collected by at least one camera, wherein the image comprises a representation of a subject and the subject is a consumer of pre-made disposable articles; determining a scale of the image that correlates dimensions of the representation of the subject in the image to physical dimensions of the subject;
determining physical attributes of the representation of the subject in the image through image processing;
based on the scale of the image and the physical attributes of the representation of the subject, determining a plurality of fit parameters for the subject;
based on an application of the plurality of fit parameters to the one or more of the plurality of disposable article sizing models, determining, by the disposable article recommendation computing system, a recommended pre-made disposable article for the subject, wherein the recommended pre-made disposable article is selected from the plurality of pre-made disposable articles available for purchase; and
providing, by the disposable article recommendation computing system, an indication of the recommended pre-made disposable article for the subject.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A computer-based method, comprising:
storing, by a disposable article recommendation computing system in data store, a plurality of disposable article three-dimensional (3D) sizing models that define dimensions of a respective plurality of pre-made disposable articles and that are configured for application to a plurality of fit parameters;

receiving, by the disposable article recommendation computing system, an image collected by at least one camera, wherein the image comprises a representation of a subject and the subject is a consumer of pre-made disposable articles;

determining, by the disposable article recommendation computing system, a scale of the image that correlates dimensions of the representation of the subject in the image to physical dimensions of the subject;

executing an error checking routine configured to ensure that the image is suitable for using for selecting one of the plurality of disposable article 3D sizing models, the error checking routine comprising determining a confidence value (1) for each joint position of the image, and/or (2) for a number of joint positions for a single joint of the image, the error routine configured to reduce error by rejecting the image and requesting a new image if error is detected based on the confidence value;

determining, by the disposable article recommendation computing system, physical attributes of the representation of the subject in the image;

based on the scale of the image and the physical attributes of the representation of the subject, determining, by the disposable article recommendation computing system, the plurality of fit parameters for the subject;

applying, by the disposable article recommendation computing system, the plurality of fit parameters, the plurality of fit parameters comprising at least a range of waist circumferences, a range of thigh circumferences, and range of rise measurements of the subject as determined from the image, to multiple different 3D bounds and sizes of each of the one or more of the plurality of disposable article 3D sizing models;

based on the application of the plurality of fit parameters to the one or more of the plurality of disposable article 3D sizing models, determining, by the disposable article recommendation computing system, a recommended pre-made disposable article for the subject, wherein the recommended pre-made disposable article is selected from the plurality of pre-made disposable articles based on the pre-made disposable article being detected as corresponding to a 3D sizing model, of the plurality of disposable 3D sizing models, the 3D sizing model having a 3D bounds and a size corresponding to the plurality of fit parameters; and displaying, by the disposable article recommendation computing system, on a display screen an indication of the recommended pre-made disposable article for the subject.

2. The computer-based method of claim 1, wherein the recommended pre-made disposable article for the subject comprises any of a recommended standard size of a pre-made disposable article, a recommended product line of a pre-made disposable article, and a recommended style of pre-made disposable article.

3. The computer-based method of claim 1, wherein the image comprises a scale object positioned proximate to the representation of the subject.

4. The computer-based method of claim 3, wherein the physical dimensions of the scale object in the image are known to the disposable article recommendation computing system.

5. The computer-based method of claim 1, wherein determining the scale of the image comprises determining an X direction scale and a Y direction scale.

6. The computer-based method of claim 1, further comprising: prior to determining the plurality of fit parameters, processing, by the disposable article recommendation computing system, the image to account for a perspective angle between the subject and the at least one camera.

7. The computer-based method of claim 1, wherein the physical attributes comprise a plurality of joint locations of the subject.

8. The computer-based method of claim 7, wherein the plurality of joint locations of the subject are determined based at least partially on a machine learning model.

9. The computer-based method of claim 1, wherein the physical attributes comprise a distance between detected aspects of the representation of the subject in the image.

10. The computer-based method of claim 1, wherein the physical attributes comprise any of a length, a width, an area, and a volume of an aspect of the representation of the subject in the image.

11. The computer-based method of claim 1, wherein the plurality of fit parameters are based on correlations to one or more of the physical attributes of the subject.

12. The computer-based method of claim 1, wherein the physical attributes comprise any of a head width, an eye separation distance, a torso length, a hip width, and a shoulder width.

13. The computer-based method of claim 1, wherein the plurality of fit parameters comprise any of an estimated waist circumference of the subject, an estimated thigh circumference of the subject, and an estimated rise measurement of the subject.

14. The computer-based method of claim 13, wherein each of the plurality of disposable article three-dimensional sizing models comprises a waist circumference range, a thigh circumference range, and a rise measurement range.

15. The computer-based method of claim 14, wherein applying the plurality of fit parameters to one or more of the plurality of disposable article three-dimensional sizing models comprises determining, for each respective disposable article three-dimensional sizing model, whether the estimated waist circumference is within the waist circumference range, the estimated thigh circumference is within the thigh circumference range, and the estimated rise measurement is within the rise measurement range.

16. The computer-based method of claim 15, wherein the recommended pre-made disposable article for the subject is one of a plurality of different pre-made disposable articles that are determined to be sized for the subject.

17. The computer-based method of claim 1, further comprising: receiving, by the disposable article recommendation computing system, one or more user supplied values.

18. The computer-based method of claim 17, wherein the user supplied values comprise any of an age of the subject, a weight of the subject, a race of the subject, a gender of the subject, a height of the subject, a gestational age of the subject at birth, and a head circumference of the subject.

19. The computer-based method of claim 17, further comprising: determining, by the disposable article recommendation computing system, a disposable article consumption prediction; and providing, by the disposable article recommendation computing system, the disposable article consumption prediction.

20. The computer-based method of claim 19, wherein the disposable article consumption prediction is based on one or more of the user supplied values.

21. The computer-based method of claim 20, wherein the disposable article consumption prediction is based on one or more of the user supplied values and one or more of the determined physical attributes.

22. The computer-based method of claim 19, wherein the disposable article consumption prediction comprises an estimated number of the recommended pre-made disposable articles to be used by the subject.

23. The computer-based method of claim 19, wherein the disposable article consumption prediction is associated with any of a product, a product size, and a product lineup.

24. The computer-based method of claim 19, wherein the disposable article consumption prediction comprises an estimated amount of time the recommended pre-made disposable article will fit the subject.

25. The computer-based method of claim 19, further comprising: sending, by the disposable article recommendation computing system, a purchase reminder notification to a remote computing device based on the disposable article consumption prediction.

\* \* \* \* \*